United States Patent
Enomura et al.

(10) Patent No.: US 10,182,975 B2
(45) Date of Patent: *Jan. 22, 2019

(54) SILICON OXIDE-COATED IRON OXIDE COMPOSITION FOR COATING COMPRISING IRON OXIDE PARTICLES COATED WITH SILICON OXIDE

(71) Applicant: M. TECHNIQUE CO., LTD., Izumi-shi, Osaka (JP)

(72) Inventors: Masakazu Enomura, Izumi (JP); Daisuke Honda, Izumi (JP)

(73) Assignee: M. TECHNIQUE CO., LTD., Izumi-shi, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/923,390

(22) Filed: Mar. 16, 2018

(65) Prior Publication Data

US 2018/0200159 A1    Jul. 19, 2018

Related U.S. Application Data

(63) Continuation of application No. 15/527,986, filed as application No. PCT/JP2016/079700 on Oct. 5, 2016, now Pat. No. 9,949,898.

(30) Foreign Application Priority Data

Oct. 5, 2015 (JP) .................................. 2015-197556
Jun. 2, 2016 (JP) .................................. 2016-111346

(51) Int. Cl.
*A61K 8/02* (2006.01)
*C01G 49/06* (2006.01)
(Continued)

(52) U.S. Cl.
CPC .............. *A61K 8/0245* (2013.01); *A61K 8/04* (2013.01); *A61K 8/19* (2013.01); *A61K 8/25* (2013.01);
(Continued)

(58) Field of Classification Search
None
See application file for complete search history.

(56) References Cited

U.S. PATENT DOCUMENTS 4,729,785 A    3/1988   Schwab et al.
5,340,393 A    8/1994   Jacobson
(Continued)

FOREIGN PATENT DOCUMENTS

JP    59-31004 A    2/1984
JP    60-135506 A   7/1985
(Continued)

OTHER PUBLICATIONS

International Search Report, issued in PCT/JP2016/079700, dated Nov. 22, 2016.
(Continued)

*Primary Examiner* — Alexandre F Ferre
(74) *Attorney, Agent, or Firm* — Birch, Stewart, Kolasch & Birch, LLP

(57) ABSTRACT

The present invention provides a composition for coating having high ultraviolet ray protection ability for a coating material, and properties required for a coating material such as texture, appearance, designability and weather resistance. The composition is a silicon oxide-coated iron oxide composition for coating comprising iron oxide particles, a primary particle diameter of which is 1 nm or more and 50 nm or less, wherein at least a part of the surface of said iron oxide particles is coated with silicon oxide, and wherein said composition comprises an iron oxide particle dispersion (Continued)

having the average molar absorption coefficient of 1500 L/(mol·cm) or more for the light of the wavelengths from 190 nm to 380 nm in a state that said coated iron oxide particles are dispersed in a dispersion medium. It is preferable that the transmittance of said iron oxide particle containing dispersion for the light of the wavelengths from 200 nm to 420 nm is 2.0% or less, and the transmittance of said iron oxide particle containing dispersion for the light of the wavelengths from 620 nm to 780 nm is 80% or more.

14 Claims, 7 Drawing Sheets

(51) Int. Cl.
  A61K 8/04    (2006.01)
  A61K 8/19    (2006.01)
  A61K 8/25    (2006.01)
  A61K 8/49    (2006.01)
  A61Q 1/02    (2006.01)
  A61Q 17/04   (2006.01)
  C09D 7/40    (2018.01)
  C09D 1/00    (2006.01)
  C09D 5/32    (2006.01)
  C01B 13/36   (2006.01)
  C01G 9/02    (2006.01)
  C09D 5/33    (2006.01)
  C08K 3/34    (2006.01)
  C09D 7/61    (2018.01)
  B82Y 30/00   (2011.01)
  C08K 3/22    (2006.01)

(52) U.S. Cl.
  CPC .............. *A61K 8/4926* (2013.01); *A61Q 1/02* (2013.01); *A61Q 17/04* (2013.01); *C01B 13/36* (2013.01); *C01G 9/02* (2013.01); *C01G 49/06* (2013.01); *C08K 3/34* (2013.01); *C09D 1/00* (2013.01); *C09D 5/004* (2013.01); *C09D 5/32* (2013.01); *C09D 7/61* (2018.01); *C09D 7/67* (2018.01); *A61K 2800/413* (2013.01); *A61K 2800/43* (2013.01); *A61K 2800/621* (2013.01); *A61K 2800/651* (2013.01); *B82Y 30/00* (2013.01); *C01P 2002/72* (2013.01); *C01P 2002/82* (2013.01); *C01P 2004/04* (2013.01); *C01P 2004/32* (2013.01); *C01P 2004/64* (2013.01); *C01P 2004/84* (2013.01); *C08K 2003/2265* (2013.01)

(56) References Cited

U.S. PATENT DOCUMENTS

| | | | |
|---|---|---|---|
| 6,235,270 | B1 | 5/2001 | Ishii et al. |
| 6,534,044 | B1 | 3/2003 | Wada et al. |
| 2002/0037262 | A1 | 3/2002 | Tanaka et al. |
| 2002/0117084 | A1 | 8/2002 | Hayashi et al. |
| 2002/0168523 | A1 | 11/2002 | Uchida et al. |
| 2010/0021712 | A1 | 1/2010 | Katayama |
| 2010/0155310 | A1 | 6/2010 | Enomura |
| 2011/0015054 | A1 | 1/2011 | Enomura |
| 2011/0101263 | A1 | 5/2011 | Tokumitsu et al. |
| 2013/0343979 | A1 | 12/2013 | Kuraki et al. |
| 2014/0027667 | A1 | 1/2014 | Rowe |
| 2014/0037519 | A1 | 2/2014 | Kuraki et al. |
| 2014/0308158 | A1 | 10/2014 | Maekawa et al. |
| 2015/0202655 | A1 | 7/2015 | Nakano et al. |
| 2015/0217332 | A1 | 8/2015 | Fujii et al. |
| 2017/0130358 | A1 | 5/2017 | Enomura |
| 2017/0213624 | A1 | 7/2017 | Ohkoshi et al. |

FOREIGN PATENT DOCUMENTS

| | | |
|---|---|---|
| JP | 61-256705 A | 11/1986 |
| JP | 7-506081 A | 7/1995 |
| JP | 9-77503 A | 3/1997 |
| JP | 2002-188021 A | 7/2002 |
| JP | 2002-308629 A | 10/2002 |
| JP | 2007-131460 A | 5/2007 |
| JP | 2008-63200 A | 3/2008 |
| JP | 2008-260648 A | 10/2008 |
| JP | 2009-82902 A | 4/2009 |
| JP | 2009-112892 A | 5/2009 |
| JP | 2009-263547 A | 11/2009 |
| JP | 2010-168468 A | 8/2010 |
| JP | 2011-94212 A | 5/2011 |
| JP | 2014-29024 A | 2/2014 |
| JP | 2014-42891 A | 3/2014 |
| JP | 2014-42892 A | 3/2014 |
| WO | WO 98/26011 A1 | 6/1998 |
| WO | WO 98/47476 A1 | 10/1998 |
| WO | WO 00/42112 A1 | 7/2000 |
| WO | WO 2008/129901 A1 | 10/2008 |
| WO | WO 2009/008392 A1 | 1/2009 |
| WO | WO 2009/008393 A1 | 1/2009 |
| WO | WO 2012/127669 A1 | 9/2012 |
| WO | WO 2012/147209 A1 | 11/2012 |
| WO | WO 2013/073695 A1 | 5/2013 |
| WO | WO 2016/009926 A1 | 1/2016 |
| WO | WO 2016/010018 A1 | 1/2016 |
| WO | WO 2016/060223 A1 | 4/2016 |

OTHER PUBLICATIONS

Japanese Notice of Reasons for Refusal for Application No. 2017-533983, dated Aug. 9, 2017, with English language translation.
Written Opinion of the International Searching Authority, issued in PCT/JP2016/079700, dated Nov. 22, 2016.

SILICON OXIDE-COATED IRON OXIDE COMPOSITION FOR COATING COMPRISING IRON OXIDE PARTICLES COATED WITH SILICON OXIDE

CROSS REFERENCE TO RELATED APPLICATIONS

This application is a Continuation of copending application Ser. No. 15/527,986, filed on May 18, 2017, which was filed as PCT International Application No. PCT/JP2016/079700 on Oct. 5, 2016, which claims the benefit under 35 U.S.C. § 119(a) to Patent Application No. 2016-111346, filed in Japan on Jun. 2, 2016 and Patent Application No. 2015-197556, filed in Japan on Oct. 5, 2015, all of which are hereby expressly incorporated by reference into the present application.

TECHNICAL FIELD

The present invention relates to silicon oxide-coated iron oxide composition for coating comprising iron oxide particles coated with silicon oxide.

BACKGROUND ART

A material for protecting ultraviolet rays is used in sunscreens, lipsticks and foundations in the cosmetics field, and exterior walls and signboards in building materials, and paints used to vehicles and the like, etc. When used as cosmetics, since they are applied directly to the skin, transparency and safety are important in addition to ultraviolet ray protection ability. Also when used as a paint, not only color vividness and designability, but also light resistance against degradation by sunlight irradiation and durability against environmental change associated with weather changes are required. Thus, a substance that protects coating materials from ultraviolet rays and the like is used to protect components contained in a paint and a coating film, in a method of mixing it in the paint or in a method of coating it on the coating film.

Generally, use of a metal oxide as a material for protecting components in the coating material from ultraviolet rays and the like is effective for such coating materials. When the metal oxide is an iron oxide, it is required to use the iron oxide in a smallest possible amount and to reduce the influence of visible light, in order not to spoil protective ability from ultraviolet rays and the like for components in the coating material, as well as a tint generated from the coating material, its chroma, color properties such as transparency, and esthetics when applied to a human body, and designability of the coated products.

As of an iron oxide for protecting a coating material, Patent Literature 1 discloses a coloring pigment for sunlight high reflecting coating, comprising red iron oxide or yellow hydrous iron oxide having an average particle diameter of 10 nm to 300 nm. Patent Literature 2 discloses an iron oxide as a needle-shaped silica-coated Bengara red pigment having an average length of 500 nm and an average diameter of 100 nm.

However, in general, when a substance is present as nanoparticles in a dispersion, it may exhibit quite different properties which cannot be predicted from the original characteristics of the material. Patent Literature 1 and Patent Literature 2 describe properties of powders of the described iron oxide or silica-coated iron oxide regarding reflectivity and color difference, but do not describe its properties as a dispersion of nanoparticles at all. Accordingly, when a paint using a dispersion wherein the silica-coated iron oxide is nanoparticulated, is used for a coating film or a coating material, it could not be predicted whether the obtained paint would exhibit both of protection against ultraviolet rays and the liken and transparency. In addition, also when the oxide particles are used for applying them to a human body, ultraviolet ray protection ability of the iron oxide itself is important. However, Patent Literature 1 and Patent Literature 2 describe the silica coating for inhibition of photocatalytic activity in the described silica-coated iron oxide, but do not describe specific silica coating for controlling ultraviolet absorptivity at all.

Further, Patent Literature 5 discloses a metal oxide comprising an iron oxide wherein the average particle diameter of the iron oxide is in the range from 0.001 µm to 1.0 µm, and the absorbance of the metal oxide sol at the solid component concentration of 0.05 wt % at the wavelength of 800 nm is 0.1 or less, and the absorbance at the wavelength of 560 nm is 0.5 or less. Patent Literature 5 suggests improvement in dispersibility and light resistance by modifying the particle surface with silica, but each Examples does not describe a silica-coated particles. Therefore, the iron oxide particles themselves have a weak absorption ability against a light in the range from 190 nm to 380 nm, the ultraviolet region including UVA, UVB and UVC, and may not be used for a coated body and the like for which application to a human body and weather resistance are required.

In a multilayer coating film and a highly designed multilayer coating film described in Patent Literature 3 or Patent Literature 4, difference between highlight and shade for a particular color is increased, and thereby intensity of the reflected light varies greatly depending on the observation angle, to realize depth feeling and dense feeling. Therefore, for a coating film comprising a coloring material such as an iron oxide, it is required to improve the transmittance for a particular color in order to enhance the highlight, and to increase difference between highlight and shade. As a molar absorption coefficient indicating ultraviolet ray absorption ability of an iron oxide is larger, it is possible to improve transparency of the coating film as an iron oxide particle dispersion, and to make the haze value smaller by reducing its amount. However, in the case of using the conventional silica-coated iron oxide as described in Patent Literatures 1 and 2, the molar absorption coefficient for the light of the wavelengths from 190 nm to 380 nm is small, and the transmittance in the visible region tends to be lower, and the haze value tends to increase, and thus designability of the multilayer coating film product are impaired.

Patent Literature 6 filed by the present applicant discloses a method of producing various nanoparticles of an iron oxide and the like between two processing surfaces being capable of approaching to and separating from each other and rotating relative to each other. However, the described iron oxide nanoparticles are the nanoparticles of black iron oxide ($Fe_3O_4$: magnetite) and yellow iron oxide (FeOOH: goethite), and it was not observed that the iron oxide nanoparticles have ultraviolet ray protection ability, or properties to transmit a visible light and to absorb an ultraviolet light. Further, in the first place, suppression of the specific characteristics expressed in oxide particles themselves has not been described, and thus, color characteristics of oxide particles themselves have not been investigated sufficiently so far. Therefore, a composition for coating is desired which can be suitably used in both aspects of ultraviolet ray protection ability and aesthetics or designability.

CITATION LIST

Patent Literature

Patent Literature 1: JP 2009-263547
Patent Literature 2: WO 1998/26011
Patent Literature 3: JP 2014-042891
Patent Literature 4: JP 2014-042892
Patent Literature 5: JP H09-077503
Patent Literature 6: WO 2009/008393

SUMMARY OF THE INVENTION

Technical Problem

In light of such circumstances, an object of the present invention is to provide a silicon oxide-coated iron oxide composition for coating, which does not spoil aesthetics when applied to a human body, or designability of a product, and is suitable for use in a coating material. Particularly, an object of the present invention is to provide a silicon oxide-coated iron oxide composition for coating comprising iron oxide particles. a primary particle diameter of which is 1 nm or more and 50 nm or less, which is effective for a coating material aiming transparency, wherein at least a part of the surface of said iron oxide particles is coated with silicon oxide, and wherein said composition comprises an iron oxide particle dispersion having, the average molar absorption coefficient of 1500 L/(mol·cm) or more for the light of the wavelengths from 190 nm to 380 nm in a state that said coated iron oxide particles are dispersed in a dispersion medium.

Solution to the Problem

The present inventors have found that iron oxide particles which molecular absorption coefficient for the ultraviolet regions is controlled., wherein at least a part of the surface of the iron oxide particles is coated with silicon oxide, is applied to a composition for coating. Then, the present inventors have accomplished the invention as follows.

Namely, the present invention provides a silicon oxide-coated iron oxide composition for coating comprising iron oxide particles, a primary particle diameter of which is 1 nm or more and 50 nm or less, wherein at least a part of the surface of said iron oxide particles is coated with silicon oxide, and wherein said composition comprises an iron oxide particle dispersion having the average molar absorption coefficient of 1500 L/(mol·cm) or more for the light of the wavelengths from 190 nm to 380 nm in a state that said coated iron oxide particles are dispersed in a dispersion medium.

In the present invention, it is preferred that said dispersion medium of the iron oxide particle dispersion wherein at least a part of the surface of the iron oxide particles is coated with silicon oxide is pure water. And in the present invention, it is preferred that said coated iron oxide particles are provided with an ester group and said dispersion medium is butyl acetate.

In the present invention, it is preferred that the molar absorption coefficient of said iron oxide particle dispersion for the light of the wavelength, of 400 nm is 500 L/(mol·cm) or more, or the molar absorption coefficient of said iron oxide particle dispersion for the light of the wavelength of 300 nm is 1500 L/(mol·cm) or more, or the molar absorption coefficient of said iron oxide particle dispersion for the light of the wavelength of 250 nm is 1500 L/(mol·cm) or more.

In the present invention, it, is preferred that the molar absorption coefficient of said iron oxide particle dispersion for the light of the wavelength of 220 nm is 2000 L/(mol·cm) or more.

In the present invention, it is preferred that the transmittance of said iron oxide particle dispersion for the light of the wavelengths from 200 nm to 420 nm is 2.0% or less, and the transmittance of said iron oxide particle dispersion for the light of the wavelengths from 620 nm to 780 nm is 80% or more. It is preferred that the haze value of said iron oxide particle dispersion is 2.0% or less at the concentration of 2 wt % of silicon oxide-coated iron oxide.

The present invention may be performed as said silicon oxide comprising amorphous silicon oxide. In the present invention, it is preferred that said iron oxide particles coated with silicon oxide is core-shell type iron oxide particles, wherein the surface of core iron oxide particles is coated with shell silicon oxide, and the primary particle diameter of said core-shell, type iron oxide particles is 100.5% or more and 190% or less relative to the primary particle diameter of said core iron oxide particles. Further, it is preferred that said iron oxide particles coated with silicon oxide are the particles wherein at least a part of the surface of one iron oxide particle or the surface of the aggregates of a plurality of iron oxide particles is coated with silicon oxide, and the particle diameter of said iron oxide particle or said aggregates of iron oxide particles is 50 nm or less, and the particle diameter of said iron oxide particles coated with silicon oxide is 100.5% or more and 190% or less, relative to said particle diameter of said iron oxide particle or said aggregates of iron oxide particles.

The present invention may be performed as said composition for coating comprising a perylene pigment.

Advantageous Effects of the Invention

The present invention enables to provide a silicon oxide-coated iron oxide composition for coating, which has a high transparency as a coating material, a high molar absorption coefficient, and an excellent ultraviolet rays protection ability. In particular, the present invention enables to provide a silicon oxide-coated iron oxide composition for coating, which does not spoil designability of a product, and can be used efficiently for a coating material, by applying iron oxide particles wherein at least a part of the surface of the iron oxide particles is coated with silicon oxide, and wherein the molar absorption coefficient for the ultraviolet region is controlled, to the composition for coating. When the molar absorption coefficient increases up to this level, designing of a composition for coating will become easier. That is, protection of ultraviolet rays is possible by blending only very small amount of the silicon oxide-coated iron oxide. It is also possible to produce a coating material having high designability from pale beige to high coloring red by utilizing red color of the iron oxide.

DESCRIPTION OF THE INVENTION

Figure 1:
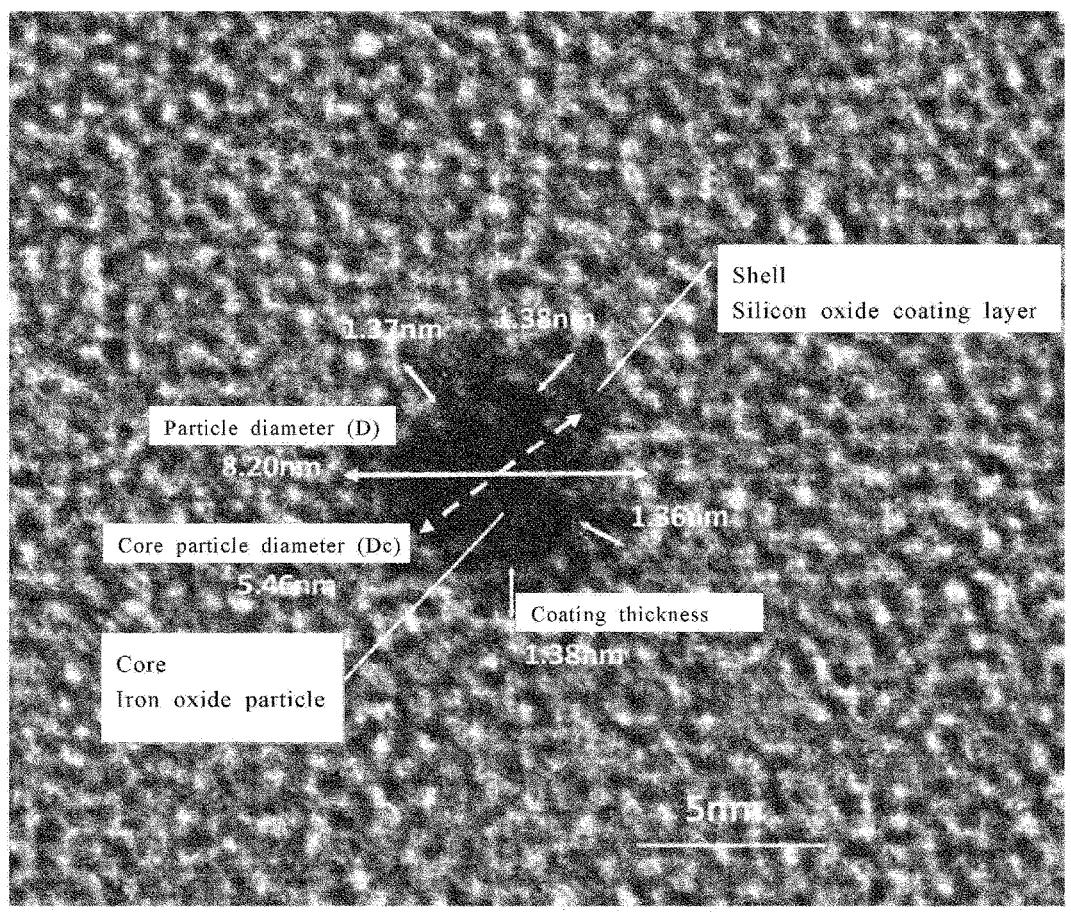
FIG. 1 shows a TEM photograph of the silicon oxide-coated iron oxide particles obtained in Example 1 of the present invention.

Hereinafter, the present invention is explained by an embodiment of the present invention based on the drawings. However, embodiments of the present invention are not limited only to the embodiment described hereinafter.

A silicon oxide-coated iron oxide composition for coating of the present invention may be used for application to skin and the like of a human body, and for application to a coating film or a coated body. Therefore, the composition has a property of protecting a human skin and a component and the like contained in a coated body from degradation. Specifically, the composition has a light resistance against degradation of a skin and a coated body by sunlight irradiation, and durability against environmental changes associated with changes in weather conditions, humidity and the like, and weather resistance to protect the coating material from photocatalytic activity. However, when the conventional, silicon oxide-coated iron oxide is applied to a composition for coating to give weather resistance, due to its low molar absorption coefficient, its amount used becomes very large. Thus, transparency of a composition for coating and color characteristics such as tint and chroma, esthetics such as texture and appearance, and designability of a product are impaired and a desired color characteristics may not be obtained. It was difficult to possess weather resistance, transparency and designability.

A silicon oxide-coated iron oxide composition for coating of the present invention includes iron oxide particles wherein at least a part of the surface of the iron oxide particles is coated with silicon oxide (hereinafter, referred to as silicon oxide-coated iron oxide particles). Silicon oxide-coated iron oxide particles of the present invention may be core-shell type silicon oxide-coated iron oxide particles wherein the entire surface of core iron oxide particles is uniformly coated with shell silicon oxide. Further, the silicon oxide-coated iron oxide particles are preferably silicon oxide-coated iron oxide particles wherein a plurality of iron oxide particles are not aggregated, and at least a part of the surface of one iron oxide particle is coated with silicon oxide. But, the silicon oxide-coated iron oxide particles may be silicon oxide-coated iron oxide particles wherein at least, a part of the surface of the aggregate wherein a plurality of iron oxide particles are aggregated, is coated with silicon oxide.

In the present invention, at least a part of the surface of iron oxide particles is coated with silicon oxide in order to improve a molar absorption coefficient as described below. Thereby, it is possible to use a composition for coating intended for transparency and gloss improvement in case of using as cosmetics, and to use a composition for coating intended for clear coating film in case of using, as a paint, and to use suitably as a composition for coating by mixing the composition with another pigment.

A silicon oxide-coated iron oxide composition for coating of the present invention. comprises powers of silicon oxide-coated iron oxide particles; a dispersion wherein silicon oxide-coated iron oxide particles are, dispersed in a liquid dispersion medium; and a dispersion wherein silicon oxide-coated iron oxide particles arc dispersed in a solid such as glass and resin, and the like. Silicon oxide-coated iron oxide particles included in the composition for coating may be composed of silicon oxide-coated iron oxide particles wherein at least a part of the surface of one iron oxide particle is coated with silicon oxide, or may be composed of silicon oxide-coated iron oxide particles wherein at least a part of the surface of the aggregates of a plurality of iron oxide particles is coated with silicon oxide, or may be composed, of both of those. Further, the silicon oxide-coated iron oxide composition may be used dispersed in cosmetics or a paint together with various pigments, or may be overcoated on a coating film. Further, the silicon oxide-coated iron oxide particles may be used as a sole pigment. A liquid dispersion medium includes water such as tap water, distilled water, RO water (reverse osmosis water), pure water and ultrapure water; an alcohol solvent such as methanol, ethanol and, isopropyl alcohol; a polyhydric alcohol solvent such as propylene glycol, ethylene glycol, diethylene glycol and glycerine; an ester solvent such as ethyl acetate and butyl acetate; an aromatic solvent such as benzene, toluene and xylene; a ketone solvent such as acetone and, methyl ethyl ketone; a nitrile solvent such as acetonitrile; silicone oil, a vegetable oil, a wax and the like. These dispersion media may be used alone or may be used by mixing a plurality of these dispersion media.

In the present invention, it is preferable that the primary particle diameter of the iron oxide particles is 1 nm or more and 50 nm or less. It is preferable that the primary particle diameter of the silicon oxide-coated iron oxide particles is 100.5% or more and 190% or less relative to the primary particle diameter of the iron oxide particles prior to coating with silicon oxide. When silicon oxide coating is too thin relative to the iron oxide particles, the effect regarding the color characteristics of the silicon oxide-coated iron oxide particles and the effect to reduce photocatalytic ability may not exhibit. Thus, it is preferable that the primary particle diameter of the silicon oxide-coated iron oxide particles is not less than 100.5% relative to the primary particle diameter of the iron oxide particles. When the coating is too thick, or when coarse aggregates are coated, control of color characteristics is difficult. Thus, it is preferable that the primary particle diameter of the silicon oxide-coated iron oxide particles is not more than 190% relative to the primary particle diameter of the iron oxide particles.

Further, silicon oxide-coated iron oxide particles of the present invention may be silicon oxide-coated iron oxide particles wherein at least a part of the surface of the aggregates wherein a plurality of the iron oxide particles are aggregated, is coated with silicon oxide. However, a silicon oxide-coated iron oxide wherein aggregates exceeding a certain size are coated with silicon oxide is not preferable, since such silicon oxide-coated iron oxide particles may not have sufficiently ultraviolet absorption and the like including molar absorption coefficient and the like and the effect of color characteristics, compared with silicon oxide-coated iron oxide particles wherein at least a part of the surface of one iron oxide particle is coated with silicon oxide. Here, the aggregates exceeding a certain size refer to those which magnitude is, for example, more than 50 nm. And, it is preferable that the primary particle diameter of the silicon oxide-coated iron oxide particles wherein at least a part of the surface of the aggregates wherein a plurality of the iron oxide particles are aggregated, is coated with silicon oxide is 100.5% or more and 190% or less relative to the primary particle diameter of the aggregates. Here, a diameter of the aggregates refers to a maximum distance between two points on the outer periphery of the aggregates.

The present inventors have found that the silicon oxide-coated iron oxide particle dispersion has higher molar absorption coefficient for an ultraviolet light than that of the conventional one, and have accomplished the present invention. The Japanese patent application No. 2015-197556 which is a priority application of the present application, discloses a silicon oxide-coated iron oxide particle dispersion, which is found to have unique properties. As disclosed in Japanese patent application No. 2016-111346, which is another priority application of the present application, the present inventors further have found the silicon oxide-coated iron oxide particle dispersion has a specific molar absorption coefficient for an ultraviolet light. Silicon oxide-coated iron oxide particles of the present invention essentially correspond to the silicon oxide-coated iron oxide particles disclosed in the Japanese patent application No. 2015-197556 which is a priority application of the present application.

Figure 7:
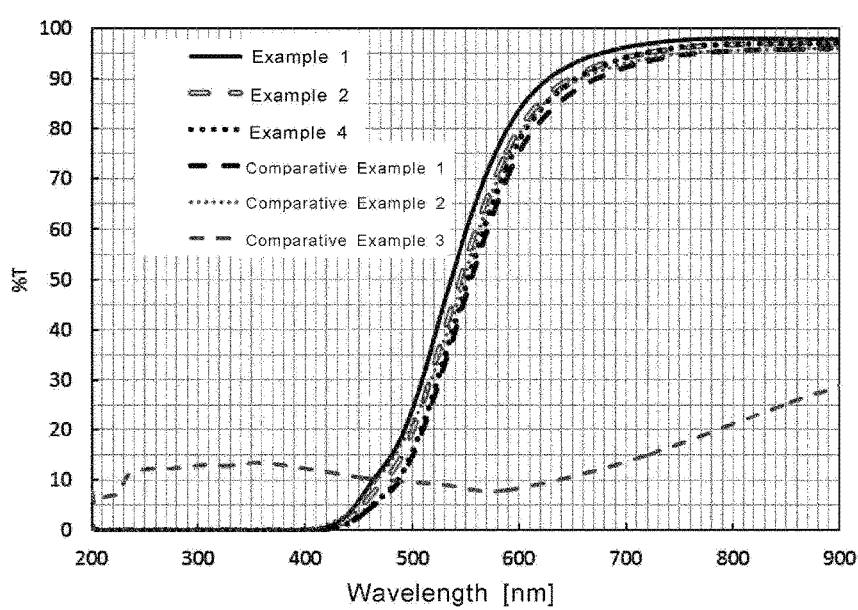
FIG. 7 shows the transmission spectra of the iron oxide particle dispersions of the silicon oxide-coated iron oxide particles obtained in Example 1 and Example 4 of the present invention, and of the iron oxide particles obtained in Comparative Example 1, Comparative Example 2 and Comparative Example 3 using pure water as a dispersion medium, and the transmission spectrum of the iron oxide particle dispersion of the silicon oxide-coated iron oxide particles obtained in Example 2 using butyl acetate as a dispersion medium.
Figure 8:
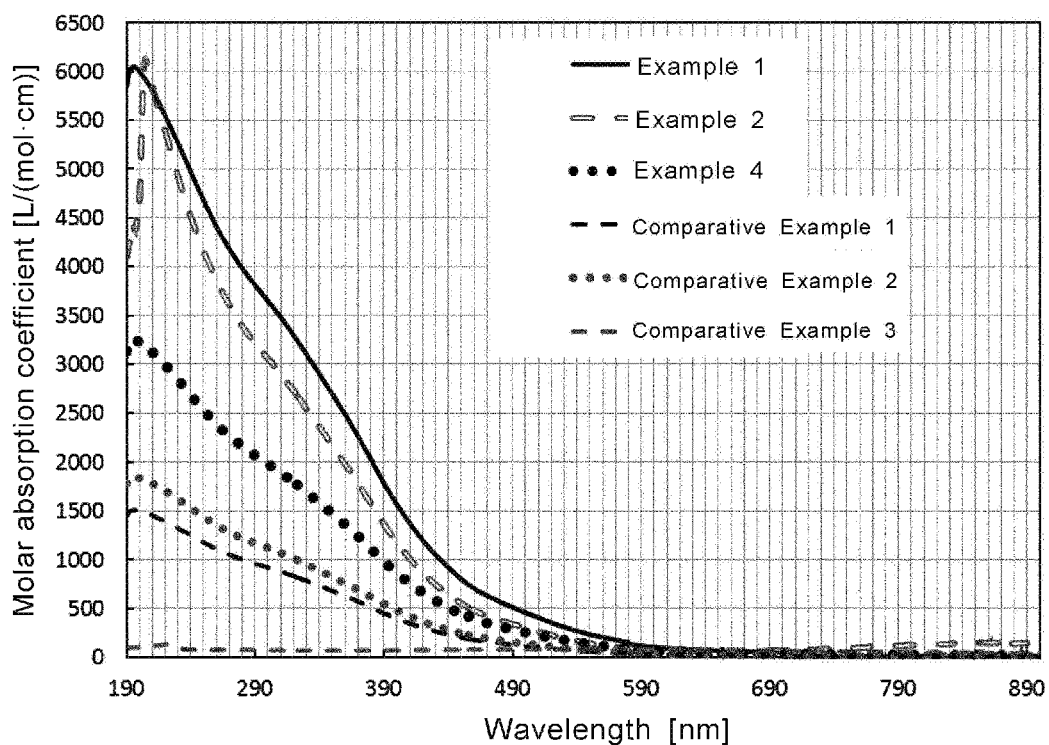
FIG. 8 shows the molar absorption coefficients of the iron oxide particle dispersions of the silicon oxide-coated iron oxide particles obtained in Example 1 and Example 4 of the present invention, and of the iron oxide particles obtained in Comparative Example 1, Comparative Example 2 and Comparative Example 3 using pure water as a dispersion medium, and the transmission spectrum of the iron oxide particle dispersion of the silicon oxide-coated iron oxide particles obtained in Example 2 using butyl acetate as a dispersion medium.

As stated below, the measurement results of the transmission spectra of the dispersions which were obtained by dispersing the silicon oxide-coated iron oxide particles obtained in Example 1 and Example 4, and the iron oxide particles or the silicon oxide-coated iron oxide particles obtained in Comparative Example 1, Comparative Example 2 and Comparative Example 3 in pure water, and the measurement result of the transmission spectrum of the dispersion which was obtained by dispersing the silicon oxide-coated iron oxide particles obtained in Example 2 in butyl acetate are shown in FIG. 7. The graph of the molar absorption coefficients at the measurement wavelength which are calculated from the absorption at each measurement wavelength for the absorption spectrum, the molar concentration of iron oxide contained in the measurement liquid, and the optical path length of the measurement sample are shown in FIG. 8 and Table 7. In the transmission spectrum and absorption spectrum, the iron oxide concentrations in the dispersion used for the measurement were the same. The iron oxide particles contained in each dispersion used for the measurement were as follows. Example 1 is the silicon oxide-coated iron oxide particles, an average primary particle diameter of which is 8.20 nm, wherein at least a part of the surface of the iron oxide particles is coated with silicon oxide. Example 2 is the silicon oxide-coated iron oxide particles, an average primary particle diameter of which is 8.19 nm, wherein the silicon oxide-coated iron oxide particles obtained in Example 1 were provided with acetyl groups. Example 4 is the silicon oxide-coated iron oxide particles, wherein at least a part of the surface of the iron oxide particles is coated with silicon oxide, wherein an average particle diameter of the silicon oxide-coated iron oxide particles is 15.46 nm, and does not exceed 50 nm. Comparative Example 1 is the iron oxide particles which surface is not coated with silicon oxide, having an average primary particle diameter of 6.40 nm. Comparative Example 2 is the silicon oxide-coated iron oxide particles, wherein at least a part of the surface of the iron oxide aggregates is coated with silicon oxide, wherein a diameter of the iron oxide aggregates exceeds 50 nm. Comparative Example 3 is the iron oxide which surface is not coated with silicon oxide, having an average primary particle diameter of 119.6 nm.

As seen in FIG. 7, almost no difference was observed between the transmittance in the visible region and the transmittance in the ultraviolet region in the dispersions using the silicon oxide-coated iron oxides and the iron oxides in Examples and Comparative Examples, except Comparative Example 3. However, as seen in FIG. 8 and Table 7, the average molar absorption coefficient of the silicon oxide-coated iron oxide composition for coating comprising the silicon oxide-coated iron oxides of Examples of the present invention, for the light of the wavelengths from 190 nm to 380 nm is 1500 L/(mol·cm) or more. But, the average molar absorption coefficient of the dispersion of the iron oxide particles of Comparative Example 1, which surface is not coated with silicon oxide, and of the dispersion of the silicon oxide-coated iron oxide of Comparative Example 2, wherein at least a part of the surface of the iron oxide aggregates is coated with silicon oxide, wherein a diameter of the iron oxide aggregates exceeds 50 nm, for the light of the wavelengths from 190 nm to 380 nm is less than 1500 L/(mol·cm).

A molar absorption coefficient is an absorption ability of a light per unit molar concentration of an iron oxide. Physical properties of particles and their dispersion generally tend to change as the particle diameter becomes smaller, and such changes cannot be predicted from the general physical properties of the materials. The present invention is characterized in that the primary particle diameter of the silicon oxide-coated iron oxide of the present invention is extremely smaller than that of the commercially available conventional silicon oxide-coated iron oxides which are generally commercialized. The present inventors unexpectedly have found that the silicon oxide-coated iron oxide particle dispersion has an ultraviolet absorptivity of a high molar absorption coefficient for an ultraviolet ray. Thereby, the silicon oxide-coated iron oxide particles can enhance an ability to protect a skin and a coated body from an ultraviolet ray, and reduce the amount of a silicon oxide-coated iron oxide composition for coating, and reduce a haze value as described below, and can properly exert performances as a silicon oxide coating iron oxide composition for coating. Of course, as described in the Japanese patent application No. 2015-197556, since photocatalytic activity is suppressed by coating at least part of the surface of iron oxide particles, decomposition of a skin, and a colorant and a resin contained in coating films and various components such as dispersing agents can be suppressed even when an ultraviolet ray is absorbed.

As described above, it is preferable that an average molar absorption coefficient of the iron oxide particles of the invention for an ultraviolet light, particularly the light of the wavelengths from 190 nm to 380 nm is 1500 L/(mol·cm) or more. It is also preferable that an average molar absorption coefficient for the light of the wavelength of 400 nm is 500 L/(mol·cm) or more, or an average molar absorption coefficient for the light of the wavelength of 300 rim is 1500 L/(mol·cm) or more, or an average molar absorption coefficient for the light of the wavelength of 250 nm is 1500 L/(mol·cm) or more. It is also preferable that an average molar absorption coefficient for the light of the wavelength of 220 nm is 2000 L/(mol·cm) or more. Thereby, such iron oxide wherein at least a part of the surface of the iron oxide is coated with silicon oxide exhibits high absorption properties in the range of the ultraviolet region of UVA (from 400 nm to 315 nm), UVB (from 315 nm to 280 nm), and UVC (less than 280 nm). Further, though it is believed that substantially no difference in primary particle diameters of the iron oxide particles of Example 1 and Comparative Example 1, the results of these Example 1 and Comparative Example 1 show that it is possible to improve a molar absorption coefficient of an iron oxide by coating at least a part of the surface with silicon oxide.

A molar absorption coefficient can be calculated from the absorbance and the molar concentration in ultraviolet-visible absorption spectrum measurement, by Formula 2 below.

$$\varepsilon = A/(c \cdot l) \quad \text{(Formula 2)}$$

In Formula 2, $\varepsilon$ is a constant determined only by the material and the wavelength, and is referred to as a molar absorption coefficient. Since it means an absorbance of a dispersion at 1 mol/L with a thickness of 1 cm, the unit is L/(mol·cm). A is an absorbance in ultraviolet-visible absorption spectrum measurement. c is a molar concentration of a sample (mol/L). l is a length through which a light is transmitted (optical path length), typically a thickness of a cell in measuring the ultraviolet-visible absorption spectrum.

Factors in improving a molar absorption coefficient in a silicon oxide-coated iron oxide of the present invention, are considered to be not only the increased surface area by the smaller primary particle diameter than that of conventional ones, but also higher crystallinity of the core iron oxide particles.

The transmittance of a dispersion including the silicon oxide-coated iron oxide particles of the invention for the light of the wavelengths from 200 nm to 420 nm is 2.0% or less, and the transmittance for the light of the wavelengths from 620 nm to 780 nm is 80% or more. The dispersion including the silicon oxide-coated iron oxide particles showing such transmittance absorbs an ultraviolet light and transmits a visible light.

The haze value of the dispersion wherein the silicon oxide-coated iron oxide particles obtained in Example 1 is dispersed in propylene glycol at a $Fe_2O_3$ concentration of 0.05 wt % is 0.00%. And, the haze value of the dispersion wherein the silicon oxide-coated iron oxide particles obtained in Example 1 is dispersed in pure water at a $Fe_2O_3$ concentration of 0.31 wt % is 0.08%. Accordingly both dispersions are highly transparent dispersions. A haze value is a numerical value indicating transparency. For example, when a composition having a haze value exceeding 2% is applied on a paint of buildings or vehicles, a color of the paint as a foundation will be impaired, and thus the desired coloring will be inhibited. Also when applied to a human skin or the like, use of a composition having a haze value exceeding 2% and a low transmittance will impair texture and appearance, which is not preferable. The present invention shows that a haze value of 2% or less of a dispersion at a $Fe_2O_3$ concentration of 2 wt % can be achieved by achieving a molar absorption coefficient of the iron oxide particle dispersion which satisfies the above properties. The haze value is more preferably 1.5% or less.

A dispersion of such silicon oxide-coated iron oxide, or a silicon oxide-coated iron oxide composition for coating prepared using the dispersion absorbs a light in the ultraviolet region, and further transmits a light in the visible region. Thus, the composition for coating can protect and guard a coating material from an ultraviolet ray, particularly the light of the wavelengths from 190 nm to 380 nm, without impairing the transparency, as used for the purpose of blending it to cosmetics or a paint, or for the purpose of protecting a clear layer for painting.

It have been found in the present invention that a molar absorption coefficient and color characteristics of a silicon oxide-coated iron oxide composition and a silicon oxide-coated iron oxide composition for coating can be controlled, by coating with silicon oxide at least a part of the surface of an iron oxide used in a silicon oxide-coated iron oxide composition for coating as shown below.

Figure 2:
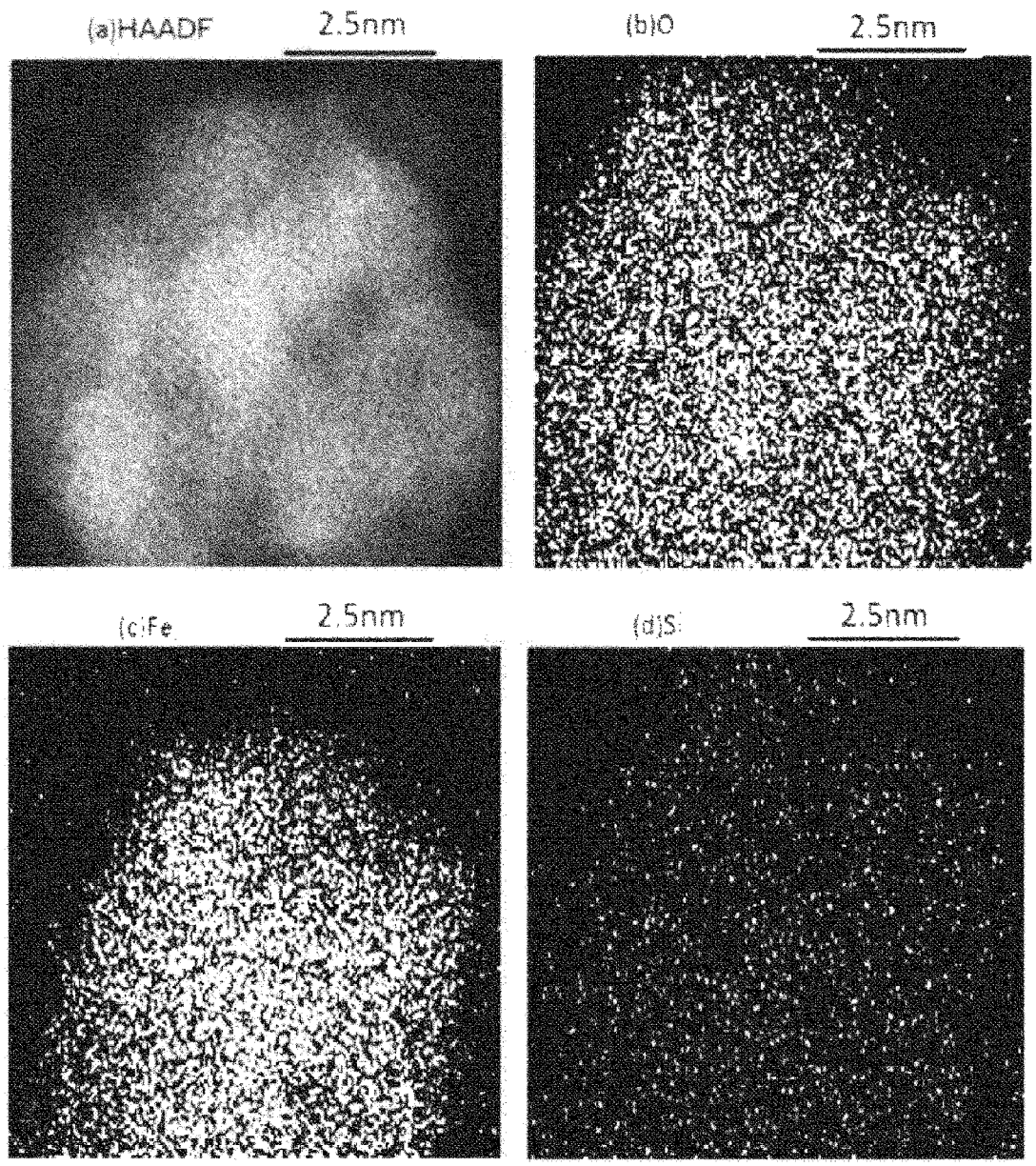
FIG. 2 shows an STEM mapping of the silicon oxide-coated iron oxide particles obtained in Example 1 of the present invention.

FIG. 1 shows a TEM photograph of the silicon oxide-coated iron oxide particles obtained in Example 1 as described below. As seen in FIG. 1, core-shell type iron oxide particles wherein the entire surface of one iron oxide particle as a core is uniformly coated with silicon oxide, is observed, and a coating layer (shell) of silicon oxide having a thickness of about 1.37 nm on the entire surface of the core iron oxide particles is observed. FIG. 2 shows a STEM mapping result of the silicon oxide-coated iron oxide particles obtained in Example 1. In FIG. 2, (a) shows a mapping of a dark-field image (HADDF image), (b) shows a mapping of oxygen (O), (c) shows a mapping of iron (Fe), and (d) shows a mapping of silicon (Si). Regarding the particles observed in the HADDF image, distribution of oxygens (O) and silicons (Si) is observed in the entire particles, and distribution of iron (Fe) is observed in about 1.37 nm smaller area in radius compared with the particles. Coating may be performed by coating at least a part of the core particles, and not entire core particles. By coating the surface of the above iron oxide with silicon oxide in the present invention, an average molar absorption coefficient of the silicon oxide-coated iron oxide particle dispersion for the light of the wavelengths from 190 nm to 380 nm can be controlled. Thus, performance in using for coating is improved, and further a haze value of the above dispersion is lowered, which are preferable. The above silicon oxide may be in the state of $SiO_2$, and also may be in the state wherein a part of oxygen is deficient like $SiO_{2-X}$.

Figure 3:
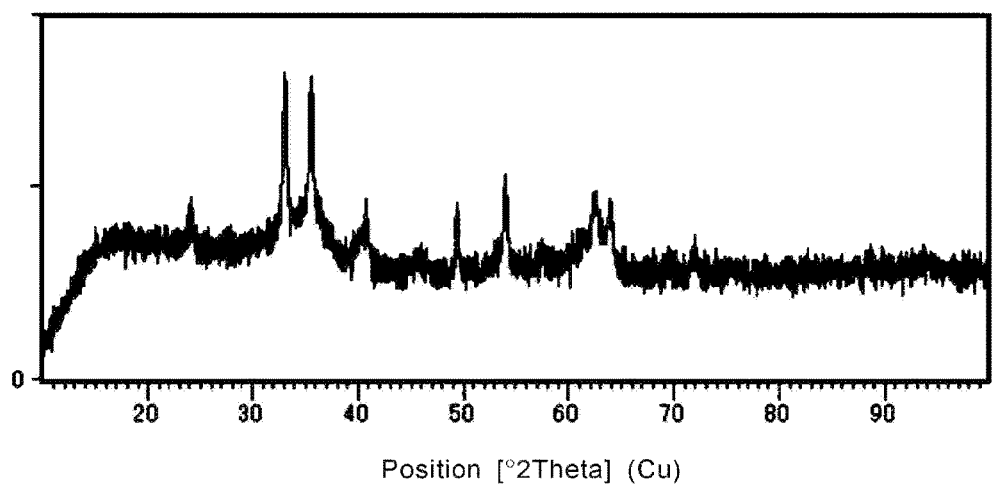
FIG. 3 shows an XRD measurement result of the silicon oxide-coated iron oxide particles obtained in Example 1 of the present invention.
Figure 4:
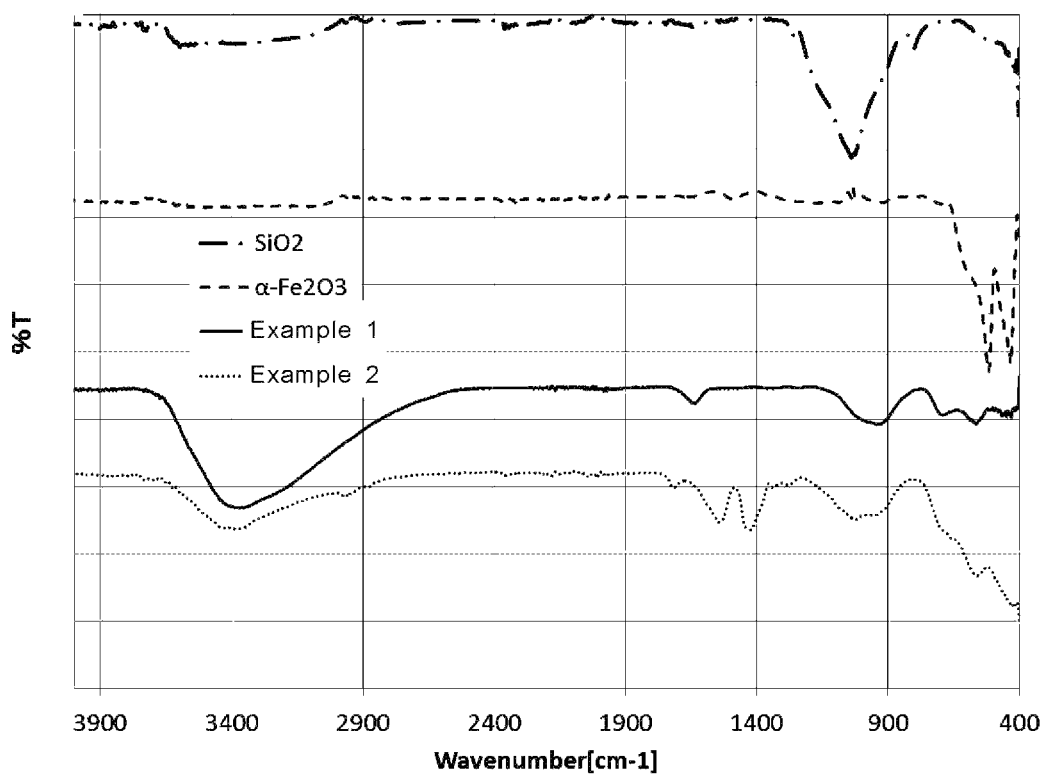
FIG. 4 shows FT-IR measurement results of the silicon oxide-coated iron oxide particles obtained in Example 1 and Example 2 of the present invention.

FIG. 3 shows an XRD measurement result of the silicon oxide-coated iron oxide particles obtained in Example 1 as described below. In the measurement result, peaks derived from the iron oxide ( -$Fe_2O_3$) are observed, but no other peaks are observed. Further, FIG. 4 shows FT-IR (infrared absorption spectrum) measurement results of the silicon oxide-coated iron oxide particles obtained in Example 1 and the silicon oxide-coated iron oxide particles obtained in Example 2, wherein the silicon oxide-coated iron oxide particles obtained in Example 1 were provided with acetyl groups, together with FT-IR measurement results of silicon dioxide ($SiO_2$) and the iron oxide ($\alpha$-$Fe_2O_3$). As seen in FIG. 4, a broad peak around 950 $cm^{-1}$ was observed for the silicon oxide-coated iron oxide particles obtained in Example 1. This peak was not observed in the iron oxide ($\alpha$-$Fe_2O_3$), and the wave number of this peak is lower than that of the peak at around 1000 $cm^{-1}$ observed in $SiO_2$.

Therefore, it is considered possible that the silicon oxide in the silicon oxide-coated iron oxide particles obtained in Example 1 is in the state of $SiO_2$ or in the state wherein a part of oxygen is deficient like $SiO_{2-X}$. Further, a broad peak from about 2900 $cm^{-1}$ to about 3600 $cm^{-1}$ derived from hydroxyl groups was observed. Also, in the FT-IR measurement result of the silicon oxide-coated iron oxide particles obtained in Example 2 wherein the silicon oxide-coated iron oxide particles obtained in Example 1 were provided with acetyl groups, the broad peak from about 2900 $cm^{-1}$ to about 3600 $cm^{-1}$ derived from hydroxyl groups is smaller, which was observed in the FT-IR measurement result of the silicon oxide-coated iron oxide particles obtained in Example 1, and peaks at about 1450 $cm^{-1}$ and about 1600 $cm^{-1}$ derived from acetyl groups were observed.

Namely, the silicon oxide-coated iron oxide particles obtained in Example 1 as described below is considered to be a silicon oxide-coated iron oxide particles wherein the surface is coated with silicon oxide. And the silicon oxide-coated iron oxide particles obtained in Example 2 is considered to be prepared by addition of an acetyl group to a hydroxyl group contained in the silicon oxide-coated iron oxide particles obtained in Example 1 to react a hydroxyl group and an acetyl group, and to add an acetoxyl group, one of ester groups to the silicon oxide-coated iron oxide particles.

Though the details are not clear, since at least a part of the surface of an iron oxide contained in a silicon oxide-coated iron oxide particle dispersion of the present invention is coated with silicon oxide, for example, aggregation of the particles are prevented by protection against absorption of a dispersion medium to the surface of the iron oxide particles, resulting in improvement of the dispersibility, and a state of the surface is in a form that an ultraviolet light is more easily absorbed, and thereby a molar absorption coefficient of a silicon oxide-coated iron oxide particles dispersion of the present invention is improved over conventional dispersions. The inventors consider the above mechanism may be one of the possibilities.

A silicon oxide-coated iron oxide particles of the present invention has (1) oxygen from the iron oxide particles, (2) iron from the iron oxide particles, (3) oxygen on the surface of the iron oxide particles, (4) silicon from the silicon oxide coating the surface of the iron particles, (5) oxygen from the silicon oxide coating the surface of the iron oxide particles. It is possible that a bond is formed between each element above, for example, the bonds: (1)-(2)-(3)-(4)-(5). Such bond may affect crystallinity of the surface of the iron oxide particles, or strain in the bond may occur, and so on. The inventors consider the above mechanism may be another possibility for control of a molar absorption coefficient of the iron oxide particles dispersion in the ultraviolet region. Not particularly limited, the inventors consider that it is another possible factor for improvement of a molar absorption coefficient of a silicon oxide-coated iron particles dispersion of the present invention, that the iron oxide particles are crystalline, and silicon oxide coating at least a part of the surface of the iron oxide particles contains amorphous one.

Further in the present invention, a molar absorption coefficient of the dispersion containing the silicon oxide-coated iron oxide may be controlled by changing a functional group contained in the silicon oxide-coated iron oxide particles. Though the details are not clear, the inventors consider that a molar absorption coefficient of the dispersion containing the silicon oxide-coated iron oxide can be controlled by controlling an element and a functional group bonding to the oxygen in above (3) or (5). For example, when hydrogen bonds to the oxygen in (3) or (5), hydroxyl groups are present on the surface of the silicon oxide-coated iron oxide particles. The hydroxyl group may be replaced by another functional group such as an acyl group, benzoyl group and an ester group. Different types of functional groups have properties of absorption and vibration against a light of a specific wavelength respectively. The properties of absorption and vibration against a light on the surface of a silicon oxide-coated iron oxide particles can be changed by changing a functional group contained in the silicon oxide-coated iron oxide particles of the present invention, including a functional group bonding to the oxygen of above (3) or (5). Therefore, the present inventors consider that a molar absorption coefficient of the dispersion containing a silicon oxide-coated iron oxide can be controlled by changing a functional group contained in a silicon oxide-coated iron oxide particles of the present invention.

Furthermore, regarding the above properties, since the particle diameter of the iron oxide particles constituting the silicon oxide-coated iron oxide particles of the present invention as well as the particle diameter of the silicon oxide-coated iron oxide particles are minute, the surface area of the silicon oxide-coated iron oxide particles increases, and a coating rate of the silicon oxide to the total silicon oxide-coated iron oxide particles is increased. Thus, the inventors consider that it would be also a possible factor for control of the molar absorption coefficient, that the above bonds: oxygen-iron-oxygen-silicon-oxygen (functional group) are increased.

In silicon oxide-coated iron oxide particles of the present invention, the color characteristics of the silicon oxide-coated iron oxide composition for coating is controlled by the existence of the silicon oxide coating at least a part of the surface of the iron oxide particles and the coating rate of the silicon oxide to the surface of the iron oxide particles. The existence of the silicon oxide coating at least a part of the surface of the iron oxide particles and the coating rate of the silicon oxide to the surface of the iron oxide particles make greater influences on a molar absorption coefficient of the silicon oxide-coated iron oxide particle dispersion for the light of the wavelengths from 190 nm to 380 nm, than on a transmission spectrum of the dispersion wherein a silicon oxide-coated iron oxide particles is dispersed in a liquid dispersion medium.

In silicon oxide-coated iron oxide particles of the present invention, a shape of the particles has smaller effects on a molar absorption coefficient than the other factors described above, and thus the shape of the particles may be, in various shapes. However, a substantially spherical shape is preferable, because the shape enables reduction of birefringence in the paint, and favorable impression in the feeling of texture and smoothness at application of cosmetics to a skin and the like. Silicon oxide-coated iron oxide particles of the present invention are preferably substantially spherical particles, wherein a long diameter/short diameter ratio is from 1.0 to 3.0, preferably from 1.0 to 2.5, more preferably from 1.0 to 2.0. Silicon oxide-coated iron oxide particles of the present, invention are preferably silicon oxide-coated iron, oxide particles, wherein at least a part of the surface of iron oxide particles which are 1 nm or more and 50 nm or less is coated with silicon oxide.

(Manufacturing Method: Device)

Figure 5:
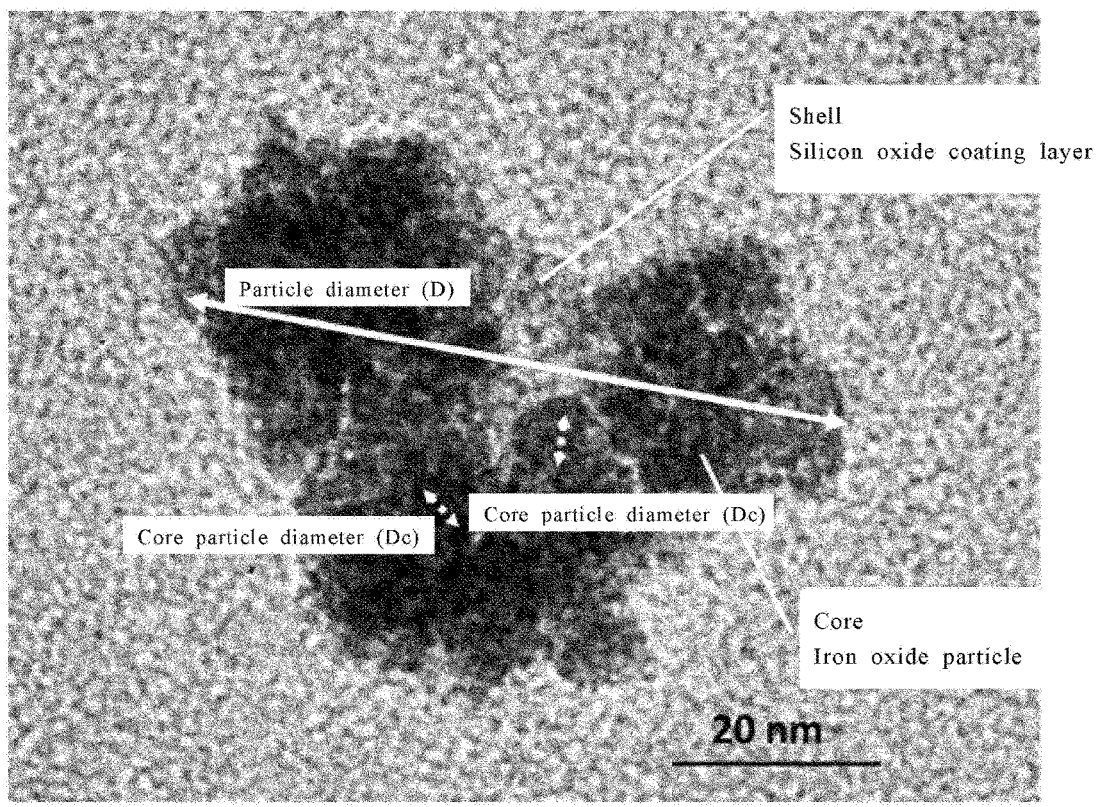
FIG. 5 shows a TEM photograph of the silicon oxide-coated iron oxide particles obtained in Comparative Example 2 of the present invention.

A method of producing silicon oxide-coated iron oxide particles of the present invention includes, for example, a method wherein iron oxide particles are produced in the first microreactor, and at least a portion of the surface of the iron oxide particles are coated with silicon oxide in the subsequent second microreactor; a method wherein iron oxide particles are produced in a batch vessel under a dilute system and the like, and continuously at least a portion of the surface, of the iron oxide particles are coated with silicon oxide under a dilute system, and the like; a method wherein iron oxide particles are produced by pulverization such as bead mill, and subsequently at least a portion of the surface of the iron oxide particles are coated with silicon oxide under a dilute system, and the like. The apparatus and method as proposed by the present applicant and described in JP 2009-112892 may be also used. The apparatus described in JP 2009-112892 comprises a stirring tank having an inner peripheral surface which cross-section is circular, and a mixing tool attached to the stirring tank with a slight gap, to the inner peripheral surface of the stirring tank, wherein the stirring tank comprises at least two fluid inlets and at least one fluid outlet; from one of the fluid inlets, the first fluid to be processed containing one of the reactants among the fluids to be processed is introduced into the stirring tank; from one fluid inlet other than the above inlet, the second fluid to be processed containing one of reactants different from the above reactant is introduced into the stirring tank through a different flow path; at least one of the stirring tank and the mixing tool rotates at a high speed relative to the other to let the above fluids be in a state of a thin film; and in the above thin film, the reactants contained in the first and second fluids to be processed are reacted. JP 2009-112892 further describes that three or more inlet tubes may be provided as shown in FIGS. 4 and 5 to introduce three or more fluids to be processed into the stirring tank.

In the present invention, it is preferable that production of iron oxide particles is preferably performed at least using a microreactor. It is preferable to use an apparatus using the same principle as the fluid processing apparatus described in Patent Literature 6, for production of iron oxide particles and for coating at least a part of the surface of the produced iron oxide particles with silicon oxide to form silicon oxide-coated iron oxide particles.

As an example of a method of producing silicon oxide-coated iron oxide particles of the present invention, it is preferable to use a method of producing silicon oxide-coated iron oxide particles, wherein iron oxide particles are precipitated in a mixed fluid of an iron oxide raw material liquid containing at least a raw material of iron oxide particles, and an iron oxide precipitation liquid containing at least iron oxide precipitation substance for precipitating iron oxide particles; and the mixed fluid containing the precipitated iron oxide particles are mixed with a silicon oxide raw material liquid containing at least a raw material of silicon oxide to coat at least a part of the surface of iron particles with silicon oxide.

A raw material of oxide iron oxide particles and a raw material of silicon oxide which are used in production of a silicon oxide-coated iron oxide particles of the present invention are not particularly limited. Any substances can be used as long as the substances become an iron oxide or silicon oxide in a manner such as a reaction, crystallization, precipitation or the like. In the present invention, hereinafter, the method above is referred to as precipitation.

A raw material of iron oxide particles includes, for example, elemental iron and an iron compound. An iron compound is not particular limited, but includes, for example, an iron salt, an iron oxide, an iron hydroxide, an iron hydroxide oxide, an iron nitride, an iron carbide, an iron complex, an iron organic salt, an iron organic complex, an iron organic compound, or a hydrate thereof, an organic solvate thereof and the like. An iron salt is not limited, but includes an iron nitrate, an iron nitrite, an iron sulfate, an iron sulfite, an iron formate, an iron acetate, an iron phosphate, an iron phosphite, an iron hypophosphite, an iron chloride, an oxy iron, an iron acetylacetonate, or a hydrate thereof, an organic solvate thereof and the like. An organic compound includes an iron alkoxide and the like. These iron compounds may be used alone, or a mixture of a plurality of these iron compounds may be used as a raw material of iron oxide particles. Specific examples include, for example, iron(III) chloride, iron(II) chloride, iron(II) nitrate, iron(III) sulfate, iron acetylacetonate and a hydrate thereof and the like.

A raw material of silicon oxide includes a silicon oxide, a silicon hydroxide, other compounds such as a silicon salt and a silicon alkoxide, and a hydrate thereof. Not particularly limited, it includes phenyltrimethoxysilane, methyltrimethoxysilane, methyltriethoxysilane, 3-glycido xypropyltrimethoxysilane, 3-trifluoropropyl-trimethoxysilane, methacryloxypropyltriethoxysilane, tetramethoxysilane (TMOS), tetraethoxysilane (TEOS), and an oligomeric condensate of TEOS, for example, ethyl silicate 40, tetraisopropylsilane, tetrapropoxysilane, tetraisobutoxysilane, tetrabutoxysilane, and a similar material thereof. Further as a raw material of silicon oxide, another siloxane compound, bis(triethoxysilyl)methane, 1,9-bis(triethoxysilyl)nonane, diethoxydichlorosilane, triethoxychlorosilane and the like may be used.

Further, when a raw material of iron oxide particles or a raw material of silicon oxide is a solid, it is preferable to use a raw material of iron oxide particles or a raw material of silicon oxide in a molten state, or in a state of being mixed or dissolved in a solvent described below, including a dispersion state. Even when a raw material of iron oxide particles or a raw materials of silicon oxide is a liquid or gas, it is preferable to use them in a state of being mixed or dissolved in a solvent described below, including a dispersion state. Regarding a raw material of iron oxide particles, in case of using only a raw material that can become iron oxide particles, iron oxide particles containing an element iron as an element other than oxygen may be produced. Further, regarding a raw material of iron oxide particles, in case of using a plurality of raw materials of iron oxide particles in addition to a raw material that can become iron oxide particles, a composite iron oxide containing a plurality of elements other than elemental iron as an element other than oxygen may be produced. Further, the invention can be performed when these iron oxide liquid and iron oxide raw material liquid and silicon oxide raw material liquid include those in a state of the condition such as dispersion or slurry.

In the present invention, iron oxide particles are preferably $\alpha$-$Fe_2O_3$ (hematite). Therefore, an iron ion contained in the raw material of iron oxide particles is preferably $Fe^{3+}$. It is preferable to use a substance that generates $Fe^{3+}$ ion in a solution as a raw material of iron oxide particles. However, a raw material of iron oxide particles may be prepared by dissolving a substance producing a $Fe^{2+}$ ion in a solvent, followed by using a means of changing the $Fe^{2+}$ ion to a $Fe^{3+}$ ion by an oxidizing acid such as nitric acid, and the like.

An iron oxide precipitation substance is not particularly limited as long as the substance can make a raw material of iron oxide particles contained in an iron oxide raw material liquid be precipitated as iron oxide particles, and can make a raw material of silicon oxide contained in an silicon oxide raw material liquid be precipitated as silicon oxide. For example, an acidic substance or a basic substance may be used. It is preferable to use an iron oxide precipitation substance at least in a state that the substance is mixed, dissolved or molecularly dispersed in a solvent described below.

A basic substance includes a metal hydroxide such as sodium hydroxide and potassium hydroxide, a metal alkoxide such as sodium methoxide and sodium isopropoxide, an amine compound such as triethylamine, diethylaminoethanol and diethylamine, ammonia and the like.

An acidic substance includes an inorganic acid such as aqua regia, hydrochloric acid, nitric acid, fuming nitric acid, sulfuric acid, fuming sulfuric acid, and an organic acid such as formic acid, acetic acid, chloroacetic acid, dichloroacetic acid, oxalic acid, trifluoroacetic acid, trichloroacetic acid and the like.

A solvent used in preparation of an iron oxide raw material liquid, an iron oxide precipitation solvent and silicon oxide raw material liquid, includes, for example, water, an organic solvent, or a mixed solvent of a plurality of these solvents. The water includes tap water, ion exchange water, pure water, ultrapure water, RO water (reverse osmosis water). The organic solvent includes, an alcohol solvent, an amide solvent, a ketone solvent, an ether solvent, an aromatic compound solvent, carbon disulfide, an aliphatic compound solvent, a nitrile solvent, a sulfoxide solvent, a halogen compound solvent, an ester solvent, an ionic liquid, a carboxylic acid compound, a sulfonic acid compound and the like. Each of the above solvents may be used alone, or a plurality of them may be mixed and used. An alcohol solvent includes a monohydric alcohol such as methanol and ethanol, a polyol such as ethylene glycol and propylene glycol, and the like. Further, if necessary, the above acidic substance or the above basic substance may be mixed with an iron oxide raw material liquid or a silicon oxide raw material liquid, as long as it does not adversely affect production of silicon oxide-coated iron oxide particles.

(Dispersing Agent and the Like)

In the present invention, various dispersing agents or surfactants may be used depending on a purpose or necessity, as long as they do not adversely affect production of silicon oxide-coated iron oxide particles. Not particularly limited, as a dispersing agent or a surfactant, various generally used commercial products or products, and newly synthesized products and the like may be used. As an example, a dispersing agent such as an anionic surfactant, a cationic surfactant, a nonionic surfactant, and various polymers and the like may be used. These may be used alone or two or more thereof may be used in combination. The surfactant and dispersing agent may be contained in at least one fluid of the iron oxide raw material liquid, iron oxide precipitation solvent, and silicon oxide raw material liquid. In addition, the surfactant and dispersing agent may be contained in another fluid different from the iron oxide raw material liquid, iron oxide precipitation solvent, and silicon oxide raw material liquid.

A method of changing a functional group contained in silicon oxide-coated iron oxide particles of the present invention is not particularly limited. It may be performed by dispersing silicon oxide-coated iron oxide particles in a desired solvent, and adding a substance containing a functional group into the dispersion liquid, followed by a processing such as stirring. It may be also performed by mixing a fluid containing silicon oxide-coated iron oxide particles and a fluid containing a substance containing a functional group using a microreactor described above.

A substance having a functional group is a substance containing a functional group that can be substituted with a hydroxyl group contained in silicon oxide-coated iron oxide particles. The examples include an acylating agent such as acetic anhydride and propionic anhydride, a methylation agent such as dimethyl sulfate and dimethyl carbonate, and a silane coupling agent such as chlorotrimethylsilane and methyl trimethoxysilane, and the like.

Not particularly limited, a silicon oxide coating iron oxide composition for coating of the present invention may be applied to those described in Patent Literature 3 or 4, and various compositions for coating to be applied to a skin such as a lipstick, a foundation and a sunscreen, various compositions for coating for coating such as a solvent-based paint, a water-based paint. A silicon oxide-coated iron oxide composition for coating, if necessary, may further comprise additives such as pigments, dyes, wetting agents, dispersing agents, color separation inhibitors, leveling agents, viscosity modifiers, anti-skinning agents, anti-gelling agents, antifoaming agents, thickeners, anti-sagging agents, antifungal agents, ultraviolet absorbers, film-forming assistant agents, surfactants, resin components, if necessary A resin component for painting purposes includes polyester resins, melamine resins, phenol resins, epoxy resins, vinyl chloride resins, acrylic resins, urethane resins, silicone resins, fluorine resins and the like. A coating material which a paint containing a silicon oxide-coated iron oxide composition for coating of the present invention is applied to, may be a single coating material composed of a single layer composition for coating, or a multilayer coating material composed of a plurality of a composition for coating such as laminated coating film as described in Patent Literature 3 or 4. A silicon oxide-coated iron oxide composition for coating of the present invention may be performed by adding it to a paint containing a pigment, or to a paint such as, a clear paint.

Color of a coating material is not particularly limited, and a silicon oxide-coated iron oxide composition for coating of the present invention may be used to a desired hue. A red color such as color having a hue from RP to YR in the Munsell hue circle; a yellow to green color such as a color having a hue from Y to BG in the Munsell hue circle: a blue to purple color such as a color having a hue from B to P in the Munsell hue circle (each of these colors includes a metallic color) can be suitably mixed in a composition for coating used in a coating material. For example, all pigments and dyes registered in the color index may be used. Among these colors, a pigment or dye constituting a red color includes, for example, a pigment or dye classified into C. I. Pigment Red in the Color Index, a pigment or dye classified into C. I. Pigment Violet or C. I. Pigment Orange in the Color Index, and the like. More specific examples include a quinacridone pigment such as C. I. Pigment Red 122 and C. I. Violet 19; a diketopyrrolopyrrole pigment such as C. I. Pigment Red 254 and C. I. Pigment Orange 73; a naphthol pigment such as C. I. Pigment Red 150 and C. I. Pigment Red 170; a perylene pigment such as C. 1. Pigment Red 123 and C. I. Pigment Red 179; and an azo pigment such as C. I. Pigment Red 144, and the like. These pigments and dyes constituting a red color may be used alone, or a plurality of these may be mixed and used. Silicon oxide-coated iron oxide particles of the present invention may be also mixed in a composition for coating alone without mixing with the above pigments and dyes and the like.

When a composition for coating of the present invention comprises a perylene pigment such as C. I. Pigment Red 123 and C. I. Pigment Red 179, a coating material can be prepared which has high chroma and a large difference between highlight and shade, for example, when used in a multilayer coating used in Patent Literature 3 or 4. Thus, it is preferable particularly in case of a red coating material.

EXAMPLE

Hereinafter, the present invention is explained in more detail with reference to Examples, but the present invention is not limited only to these examples. In the following Examples, a pure water of conductivity of 0.86 μS/cm (measurement temperature: 25° C.) was used as a pure water.

(Preparation of TEM Observation Sample and Preparation of STEM Observation Sample)

A part of the wet cake samples of the silicon oxide-coated iron oxide particles after the washing process obtained in Examples was dispersed in propylene glycol, and further was diluted to 100-fold by isopropyl alcohol (IPA). The resulting diluted liquid was dropped to a collodion membrane or a micro grid, and dried to prepare a TEM observation sample or an STEM observation sample.

(Transmission Electron Microscopy and Energy Dispersive X-Ray Analyzer: TEM-EDS Analysis)

For observation and quantitative analysis of the silicon oxide-coated iron oxide particles by TEM-EDS analysis, the transmission electron microscopy JEM-2100 (JEOL Ltd.) equipped with the energy dispersive X-ray analyzer JED-2300 (JEOL Ltd.) was used. The observation condition was the acceleration voltage of 80 kV, and the observation magnification of 10,000 times or more. The particle diameters (D) described in Tables 2 and 4 which correspond to the particle diameter described in the present specification and the claims, were calculated from the maximum distance between two points on the outer periphery of the silicon oxide-coated iron oxide particles, and the average value of the measured particle diameters of 100 particles was shown. Also the core particle diameter (Dc) described in Table 2 which is the primary particle diameter of the core iron oxide or the particle diameter of the core aggregate, were calculated from the maximum distance between two points on the outer periphery of the core iron oxide particle in the silicon oxide-coated iron oxide particles, and the average value of the measured core particle diameters of 100 particles was shown. Also EDS analysis on one particle was performed, and a molar ratio between the elements contained in the core iron oxide particles and the elements contained in the shell silicon oxide was calculated. The thickness of the shell silicon oxide (hereinafter referred to as the thickness of the shell layer) was measured. Four thickness was measured for one particle, and the average value of the measured thickness of 10 particles was described in the item "coating thickness" in Table 2. Hereinafter, the core iron oxide particles are also referred to as a core, and the shell silicon oxide is also referred to as a shell or a shell layer. The core conversion particle diameter Dc described in Table 4 is the maximum distance between two points on the outer periphery of the aggregate of the core iron oxide particles.

(Scanning Transmission Electron Microscopy and Energy Dispersive X-ray Analyzer: STEM-EDS Analysis)

For the mapping and quantification of elements contained in the silicon oxide-coated iron oxide particles by STEM-EDS analysis, the atomic resolution analytical electron microscopy JEM-ARM200F (JEOL Ltd.) equipped with the energy dispersive X-ray analyzer Centurio (JEOL Ltd.) was used. The observation condition was the acceleration voltage of 80 kV and the observation magnification of 50,000 times or more, and a beam diameter of 0.2 nm was used for analysis.

(X-ray Diffraction Measurement)

For the X-ray diffraction (XRD) measurement, the powder X-ray diffractometer Empyrean (Spectris Co., Ltd., PANalytical Division) was used. The measurement condition was measurement range of 10 to 100 [°2Theta], Cu anticathode, tube voltage of 45 kV, tube current of 40 mA, and scanning speed of 0.3°/min. The XRD was measured using the dry powder of the silicon oxide-coated iron oxide particles obtained in each Example.

(FT-IR Measurement)

For the FT-IR measurement, the Fourier transform infrared spectrophotometer FT/IR-4100 (JASCO Corporation) was used. The measurement condition was the resolution of 4.0 cm$^{-1}$ and accumulated number of 1024 times, using an ATR method.

(Transmission Spectrum and Absorption Spectrum)

For the transmission spectrum and the absorption spectrum, the ultraviolet-visible absorption spectrophotometer (product name: UV-2450, Shimadzu Corporation) was used. The measurement range of the transmission spectrum was from 200 nm to 800 nm, and the measurement range of the absorption spectrum was from 190 nm to 800 nm, and the sampling rate was 0.2 nm, and the measurement speed was slow speed.

For the transmission spectrum, the dispersion liquids prepared by dispersing the silicon oxide-coated iron oxide of Examples and Comparative Examples except for Example 2 in pure water at a $Fe_2O_3$ concentration of 0.05 wt % were used as a measurement sample. The dispersion liquid prepared by dispersing the silicon oxide-coated iron oxide of Example 2 in butyl acetate dispersion at a $Fe_2O_3$ concentration of 0.05 wt % was used as a measurement sample.

For the absorption spectrum, the dispersion liquid prepareds by dispersing the silicon oxide-coated iron oxide of Examples and Comparative Examples except for Example 2 in pure water at a $Fe_2O_3$ concentration of 0.007 wt % (0.0005 mol/L) were used as a measurement sample. The dispersion liquid prepared by dispersing the silicon oxide-coated iron oxide of Example 2 in butyl acetate dispersion at a $Fe_2O_3$ concentration of 0.007 wt % (0.0005 mol/L) was used as a measurement sample. After measuring the absorption spectrum, the molar absorption coefficient at each measurement wavelength was calculated from the absorbance obtained from the measurement result and the iron oxide concentration (as $Fe_2O_3$) in the dispersion liquid, and the graph was prepared showing the measurement wavelength on the horizontal axis and the molar absorption coefficient on vertical axis. A liquid cell of thickness of 1 cm was used for measurements. Also, the molar absorption coefficients measured at a plurality of wavelengths from 190 nm to 380 nm were simply averaged so that the average molar absorption coefficient was calculated.

(Haze Value Measurement)

For the haze value measurement, the haze value meter (Model HZ-V3, Suga Test Instruments Co., Ltd.) was used. The optical condition was the double-beam method and D65 light as a light source which corresponds to JIS K 7136 and JIS K 7361. A liquid cell of thickness of 1 mm was used for measurements, and the dispersed liquids described below were measured.

Example 1

The iron oxide raw material liquid, the iron oxide precipitation solvent, and the silicon oxide raw material liquid were prepared using the high-speed rotary dispersion emulsification apparatus CLEAMIX (product name: CLM-2.2 S, M. Technique Co., Ltd.). Specifically, based on the formulation of the iron oxide raw material liquid shown in Example 1 of Table 1, the components of the iron oxide raw material liquid were mixed homogeneously by stirring using CLEARMIX at preparation temperature of 40° C. and at the rotor rotational speed of 20000 rpm for 30 min to prepare the iron oxide raw material liquid. Based on the formulation of the iron oxide precipitation solvent shown in Example 1 of Table 1, the components of the iron oxide precipitation solvent were mixed homogeneously by stirring using CLEARMIX at preparation temperature of 45° C. and at the rotor rotational speed of 15000 rpm for 30 min to prepare the iron oxide precipitation solvent. Furthermore, based on the first formulation of the silicon oxide raw material liquid shown in Example 1 of Table 1, the components of the silicon oxide raw material liquid were mixed homogeneously by stirring using CLEARMIX at preparation temperature of 20° C. and at the rotor rotational speed of 6000 rpm for 10 min to prepare the silicon oxide raw material liquid.

Regarding the substances represented by the chemical formula and abbreviations set forth in Table 1, 97 wt % $H_2SO_4$ is concentrated sulfuric acid (Kishida Chemical Co., Ltd.), NaOH is sodium hydroxide (Kanto Chemical Co., Inc.), TEOS is tetraethyl orthosilicate (Wako Pure Chemical Industry Ltd.), and $Fe(NO_3)_3$ $9H_2O$ is iron nitrate nonahydrate (Kanto Chemical Co., Inc.).

Then, the prepared iron oxide raw material liquid, the iron oxide precipitation solvent oxide and the silicon oxide raw material liquid were mixed using the fluid processing apparatus described in Patent Literature 6 filed by the present applicant. Here, the fluid processing apparatus described in Patent Literature 6 is an apparatus described in FIG. 1(B) of Patent Literature 6, wherein the openings d20 and d30 of the second and third introduction parts have concentric annular shapes which are surrounding the central opening of the processing surface 2 which is a ring-shaped disc, which was used. Specifically, the iron oxide raw material liquid as liquid A was introduced from the first introduction part dl into the space between the processing surfaces 1 and 2, and while driving the processing member 10 at a rotational speed of 1130 rpm, the iron oxide precipitation solvent as liquid B was introduced from the second introduction part d2 into the space between the processing surfaces 1 and 2, and the iron oxide raw material liquid and the iron oxide precipitation solvent were mixed in the thin film fluid, to let the core iron oxide particles be precipitated in the space between the processing surfaces 1 and 2. Then, the silicon oxide raw material liquid as liquid C was introduced from the third introduction part d3 into the space between the processing surfaces 1 and 2, and liquid C was mixed with a mixed fluid containing the core iron oxide particles in the thin film fluid. Silicon oxide was precipitated on the surface of the core iron oxide particles. The discharge liquid containing the silicon oxide-coated iron oxide particles (hereinafter, the silicon oxide-coated iron oxide particle dispersion liquid) was discharged from the space between the processing surfaces 1 and 2 of the fluid processing apparatus. The silicon oxide-coated iron oxide particle dispersion liquid was collected in the beaker b through the vessel v.

Table 2 shows the operating conditions of the fluid processing apparatus. The introduction temperatures (liquid sending temperatures) and the introduction pressures (liquid sending pressures) of liquid A, liquid B and liquid C shown in Table 2 were measured using a thermometer and a pressure gauge provided in a sealed inlet path leading to the space between the processing surfaces 1 and 2 (the first introduction part dl, the second introduction part d2 and the third introduction part d3). The introduction temperature of liquid A shown in Table 2 is the actual temperature of liquid A under the introduction pressure in the first introduction part dl. Similarly, the introduction temperature of liquid B shown in Table 2 is the actual temperature of liquid B under the introduction pressure in the second introduction part d2. The introduction temperature of liquid C shown in Table 2 is the actual temperature of liquid C under the introduction pressure in the third introduction part d3.

For the pH measurement, the pH meter, model number D-51 manufactured by HORIBA Ltd. was used. The pH of liquid A, liquid B and liquid C were measured at room temperature prior to introduction into the fluid processing apparatus. Further, it is difficult to measure the pH of the mixed fluid immediately after mixing the iron oxide raw material liquid and the iron oxide precipitation solvent, and the pH of the mixed fluid immediately after mixing the fluid containing the core iron oxide particles and the silicon oxide raw material liquid. Therefore, the silicon oxide-coated iron oxide particle dispersion liquid was discharged from the apparatus and collected in a beaker b, and the pH of the liquid was measured at room temperature.

Dry powders and wet cake samples were produced from the silicon oxide-coated iron oxide particle dispersion liquid which was discharged from the fluid processing apparatus, and collected in a beaker b. The manufacturing method was conducted according to a conventional method of this type of processing. The discharged silicon oxide-coated iron oxide particle dispersion liquid was collected, and the silicon oxide-coated iron oxide particles were settled, and the supernatant was removed. Thereafter, the silicon oxide-coated iron oxide particles were washed and settled three times repetitively with the mixed solvent of 100 parts by weight of pure water and 100 parts by weight of methanol, and then, were washed and settled three times repetitively with pure water. A part of the finally obtained wet cake of the silicon oxide-coated iron oxide particles was dried at 25° C. at -0.10 MPaG for 20 hours to obtain the dry powders. The rest was the wet cake sample.

TABLE 1

| Example 1 | | | | | | | | | | | | |
|---|---|---|---|---|---|---|---|---|---|---|---|---|
| Formulation of the 1st fluid (liquid A) Iron oxide raw material liquid | | | | Formulation of the 2nd fluid (liquid B) Iron oxide precipitation solvent | | | | Formulation of the 3rd fluid (liquid C) | | | | |
| Formulation [wt %] | | | | Formulation [wt %] | | | | Formulation [wt %] | | | | |
| Raw material | Raw material | pH | | Raw material | Raw material | pH | | Raw material | Raw material | Raw material | pH | |
| [wt %] | [wt %] | pH | [° C.] | [wt %] | [wt %] | pH | [° C.] | [wt %] | [wt %] | [wt %] | pH | [° C.] |
| $Fe(NO_3)_3$ $9H_2O$ | Pure water [98.00] | 1.8 | 26.6 | NaOH [9.00] | Pure water [91.00] | >14 | — | Pure water [92.89] | 97 wt % $H_2SO_4$ | TEOS [2.00] | <1 | — |

TABLE 1-continued

Example 1

| Formulation of the 1st fluid (liquid A) Iron oxide raw material liquid | | | | Formulation of the 2nd fluid (liquid B) Iron oxide precipitation solvent | | | | Formulation of the 3rd fluid (liquid C) — | | | | |
|---|---|---|---|---|---|---|---|---|---|---|---|---|
| Formulation [wt %] | | | | Formulation [wt %] | | | | Formulation [wt %] | | | | |
| Raw material [wt %] | Raw material [wt %] | pH | pH [° C.] | Raw material [wt %] | Raw material [wt %] | pH | pH [° C.] | Raw material [wt %] | Raw material [wt %] | Raw material [wt %] | pH | pH [° C.] |
| [2.00 wt %] | wt %] | | | wt %] | wt %] | | | wt %] | [5.11 wt %] | wt %] | | |

TABLE 2

Example 1

| Introduction flow rate [ml/min] | | | Introduction temperature (liquid sending temperature) [° C.] | | | Introduction pressure (liquid sending pressure) [MPaG] | | | Discharged liquid | |
|---|---|---|---|---|---|---|---|---|---|---|
| Liquid A | Liquid B | Liquid C | Liquid A | Liquid B | Liquid C | Liquid A | Liquid B | Liquid C | pH | Temperature [° C.] |
| 400 | 50 | 100 | 142 | 86 | 89 | 0.451 | 0.50 | 0.50 | 12.14 | 32.9 |

| Coating thickness [nm] | Shell/Core $SiO_2/Fe_2O_3$ Molar ratio | | Particle diameter (D) [nm] | Core particle diameter (Dc) [nm] | D/Dc |
|---|---|---|---|---|---|
| | Calcurated value | EDS | | | |
| 1.37 | 0.97 | 0.97 | 8.20 | 5.46 | 150.2% |

The molar ratios (shell/core) described, in Table 2 and Table 4 are the ratio of the oxides of the elements, which the molar ratio of the elements calculated by the TEM-EDS analysis on one silicon oxide-coated iron, oxide particle is converted into. For example, the molar ratio (shell/core, $SiO_2/Fe_2O_3$) in Example 1 of Table 2 is the value of $SiO_2/Fe_2O_3$ converted from the molar ratio of Si/Fe calculated by with TEM-EDS analysis on one silicon oxide-coated iron oxide particle. Table 2 shows the average molar ratio ($SiO_2/Fe_2O_3$) of 10 particles together with its calculated value. The calculated value was calculated from the Fe concentration in the iron oxide raw material liquid for core and its introduction flow rate, and the Si concentration in the silicon oxide raw material liquid for shell and its introduction flow rate.

FIG. 1 shows a TEM photograph of the silicon oxide-coated iron oxide particles obtained in Example 1. Core-shell type iron oxide particles wherein the core was one iron oxide particle, and the entire surface of the core was uniformly coated with silicon oxide, were observed, and a coating layer (shell) of silicon oxide having a thickness of about 1.37 nm on the entire surface of the core iron oxide particle was observed. In the silicon oxide-coated iron oxide particles obtained in Example 1, the core particle diameter (Dc) is 5.46 nm, and the particle diameter (D) is 8.20 nm. FIG. 2 shows a mapping result using STEM of the silicon oxide-coated iron oxide particles obtained in Example 1. In FIG. 2, (a) shows a mapping of a dark-field image (HADDF image), (b) shows a mapping of oxygen (O), (c) shows a mapping of iron (Fe), and (d) shows a mapping of silicon (Si). Regarding the observed particles in the HADDF image, distribution of oxygens (O) and silicons (Si) in the entire particles was observed, and distribution of iron (Fe) in about 1.37 nm smaller area in radius compared with the particles was observed. D/Dc was 150.2%.

Example 2

The following process was performed to impart acetyl groups as one of the ester groups to the silicon oxide-coated iron oxide particles obtained in Example 1. First, 1 part by weight of the silicon oxide-coated iron oxide particles obtained in Example 1 was added to 99 parts by weight of propylene glycol, and dispersed using the high-speed rotary dispersion emulsification apparatus CLEARMIX (product name: CLM-2.2 S, M technique Co., Ltd.) at 65° C. at the rotor rotation speed of 20000 rpm for 1 hour, to prepare a dispersion. To the obtained propylene glycol dispersion of the silicon oxide-coated iron oxide particles, were added 2 parts by weight of pyridine and 1 part by weight of acetic anhydride relative to 1 part by weight of the silicon oxide-coated iron oxide particles, and were dispersed using the above high-speed rotary dispersion emulsification apparatus at 65° C. at a rotor rotational speed of 20000 rpm for 1 hour. The resulting processed liquid was centrifuged at the condition of 26,000 G for 15 min, and the supernatant was separated to obtain the precipitates. A part of the precipitates was dried at −0.10 MPaG at 25° C. for 20 hours to obtain the dried powders. As a result of TEM observation, the core particle diameter (Dc) of the silicon oxide-coated iron oxide particles obtained in Example 2 was 5.47 nm, and the particle diameter (D) was 8.19 nm. Thus, it was confirmed that the particle diameter was substantially the same to that in Example 1. D/Dc was 149.7%.

In the XRD measurement result of the silicon oxide-coated iron oxide particles obtained in Example 1 as shown in FIG. 3, peaks derived from the iron oxide ($\alpha$-$Fe_2O_3$) were observed, but no other peaks were observed. The XRD measurement results of the silicon oxide-coated iron oxide particles obtained in Example 2 were similar to those of the silicon oxide-coated iron oxide particles in Example 1. Further, FIG. 4 shows FT-IR (infrared absorption spectrum) measurement results of the silicon oxide-coated iron oxide particles obtained in Example 1 and the silicon oxide-coated iron oxide particles obtained in Example 2, wherein the silicon oxide-coated iron oxide particles obtained in Example 1 were provided with acetyl groups, together with FT-IR measurement results of silicon dioxide ($SiO_2$) and an iron oxide ($\alpha$-$Fe_2O_3$). As seen in FIG. 4, a broad peak around 950 $cm^{-1}$ was observed for the silicon oxide-coated iron oxide particles obtained in Example 1. This peak was not observed in the iron oxide ($\alpha$-$Fe_2O_3$), and the wave number of this peak is lower than that of the peak at around 1000 $cm^{-1}$ observed in $SiO_2$. Therefore, it is considered possible that the silicon oxide in the silicon oxide-coated iron oxide particles obtained in Example 1 is in the state of $SiO_2$ or in the state wherein a part of oxygen is deficient like $SiO_{2-X}$. Further, a broad peak from about 2900 $cm^{-1}$ to about 3600 $cm^{-1}$ derived from hydroxyl groups was observed. Also, in the FT-IR measurement result of the silicon oxide-coated iron oxide particles obtained in Example 2 wherein the silicon oxide-coated iron oxide particles obtained in Example 1 were provided with acetyl groups, the broad peak from about 2900 $cm^{-1}$ to about 3600 $cm^{-1}$ derived from hydroxyl groups is smaller, which was observed in the FT-IR measurement result of the silicon oxide-coated iron oxide particles obtained in Example 1, and peaks at about 1450 $cm^{-1}$ and about 1600 $cm^{-1}$ derived from acetyl groups were observed.

Namely, the silicon oxide-coated iron oxide particles obtained in Example 1 is a silicon oxide-coated iron oxide particles wherein the surface is coated with amorphous silicon oxide. And the silicon oxide-coated iron oxide particles obtained in Example 2 is considered to be prepared by addition of an acetyl group to the silicon oxide-coated iron oxide particles obtained in Example 1 by replacing a hydroxyl group contained in the silicon oxide-coated iron oxide particles with an acetyl group.

Comparative Example 1

In Comparative Example 1, the iron oxide particles which surface was not coated by silicon oxide was prepared in the same manner as in Example 1 except that the silicon oxide raw material liquid as liquid C was not used (except the liquid C condition). TEM observation and XRD were measured in a similar manner as in Example 1. The particle diameter measured by the same method as for the core particle diameter in Example 1 was 6.40 nm. From the XRD measurement result, only the peak of iron oxide was detected. The pH of the discharged liquid was 13.89 (measurement temperature 29.6° C.). The resulting iron oxide particles in the iron oxide particle dispersion liquid had already been aggregated.

Example 3

In Example 3, the silicon oxide-coated iron oxide particles were prepared in the same manner as in Example 1 except for using an apparatus described in JP 2009-112892, and using a method of mixing and reacting liquid A (iron oxide raw material liquid), liquid B (iron oxide precipitation solvent) and liquid C (silicon oxide raw material liquid). Here, the apparatus of JP 2009-112892 is an apparatus described in FIG. 4 of JP 2009-112892, wherein the inner diameter of the stirring tank is uniform and is 420 mm, and the gap between the outer end of the mixing tool and the inner peripheral surface of the stirring tank is 1 mm, and the rotor rotational speed of the stirring blade was the same as the rotor rotational speed (1130 rpm) of the processing member 10 in the fluid processing apparatus used in Example 1. Further, liquid A was introduced into the stirring tank, and liquid B was added, mixed and reacted in the thin film consisting of liquid A that was crimped to the inner peripheral surface of the stirring tank. Then, liquid C was added, mixed and reacted in the thin film consisting of the mixed liquid of liquid A and liquid B crimped to the inner peripheral surface of the stirring tank. As a result of TEM observation, the core was one iron oxide particle, and the silicon oxide-coated iron oxide particles wherein a part of the surface of the core was coated with silicon oxide, was observed. A coating layer (shell) of silicon oxide having a thickness of from 1.0 nm to 2.0 nm on the surface of the core iron oxide particle was observed. A mapping using STEM of the silicon oxide-coated iron oxide particles obtained in Example 3, was done in the same manner as in Example 1. Regarding the observed particles in the HADDF image, distribution of oxygens (O) in the entire particles was observed, and distribution of iron (Fe) in about 1.0 nm to 2.0 nm smaller area in radius compared with the particles was observed, and distribution of silicons (Si) mainly in the coating layers was observed. The particle diameter (D) was 16.9 nm, the thickness of silicon oxide of a shell (coating thickness) was from 1.0 nm to 2.0 nm, and D/Dc of the silicon oxide-coated iron oxide particles was from 113.4% to 131.0%. From the XRD measurement results of the silicon oxide-coated iron oxide particles in Example 3, peaks derived from iron oxide ($Fe_2O_3$) were observed, and no other peaks were observed.

Example 4

The iron oxide raw material liquid, the iron oxide precipitation solvent, and the silicon oxide raw material liquid were prepared using the high-speed rotary dispersion emulsification apparatus CLEAMIX (product name: CLM-2.2 S, M. Technique Co., Ltd.). Specifically, based on the formulation of the iron oxide raw material liquid shown in Example 4 of Table 3, the components of the iron oxide raw material liquid were mixed homogeneously by stirring using CLEARMIX at preparation temperature of 40° C. and at the rotor rotational speed of 20000 rpm for 30 min to prepare the iron oxide raw material liquid. Based on the formulation of the iron oxide precipitation solvent shown in Example 4 of Table 3, the components of the iron oxide precipitation solvent were mixed homogeneously by stirring using CLEARMIX at preparation temperature of 45° C. and at the rotor rotational speed of 15000 rpm for 30 min to prepare iron oxide precipitation solvent. Furthermore, based on the formulation of the silicon oxide raw material liquid shown in Example 4 of Table 3, the components of the silicon oxide raw material liquid were mixed homogeneously by stirring using CLEARMIX at preparation temperature of 20° C. and at the rotor rotational speed of 6000 rpm for 10 min to prepare the silicon oxide raw material liquid.

Regarding the substances represented by the chemical formula and abbreviations set forth in Table 3, 97 wt % $H_2SO_4$ is concentrated sulfuric acid (Kishida Chemical Co., Ltd.), NaOH is sodium hydroxide (Kanto Chemical Co., Inc.), TEOS is tetraethyl orthosilicate (Wako Pure Chemical Industry Ltd.), and $Fe(NO_3)_3$ $9H_2O$ is iron nitrate nonahydrate (Kanto Chemical Co., Inc.).

TABLE 3

Example 4

| Formulation of the 1st fluid (liquid A) Iron oxide raw material liquid | | | | Formulation of the 2nd fluid (liquid B) Iron oxide precipitation solvent | | | | Formulation of the 3rd fluid (liquid C) | | | | |
|---|---|---|---|---|---|---|---|---|---|---|---|---|
| Formulation [wt %] | | | | Formulation [wt %] | | | | Formulation [wt %] | | | | |
| Raw material [wt %] | Raw material [wt %] | pH | pH [° C.] | Raw material [wt %] | Raw material [wt %] | pH | pH [° C.] | Raw material [wt %] | Raw material [wt %] | Raw material [wt %] | pH | pH [° C.] |
| $Fe(NO_3)_3$ $9H_2O$ [2.00 wt %] | Pure water [98.00 wt %] | 1.8 | 26.6 | NaOH [9.00 wt %] | Pure water [91.00 wt %] | >14 | — | Pure water [93.64 wt %] | 97 wt % $H_2SO_4$ [3.86 wt %] | TEOS [2.50 wt %] | <1 | — |

TABLE 4

Example 4

| Introduction flow rate [ml/min] | | | Introduction temperature (liquid sending temperature) [° C.] | | | Introduction pressure (liquid sending pressure) [MPaG] | | | Discharged liquid | |
|---|---|---|---|---|---|---|---|---|---|---|
| Liquid A | Liquid B | Liquid C | Liquid A | Liquid B | Liquid C | Liquid A | Liquid B | Liquid C | pH | Temperature [° C.] |
| 900 | 100 | 150 | 140 | 80 | 60 | 0.432 | 0.55 | 5.00 | 12.29 | 34.6 |

| Coating thickness [nm] | Shell/Core $SiO_2/Fe_2O_3$ Molar ratio | | Particle diameter (D) [nm] | Core particle diameter (Dc) [nm] | D/Dc |
|---|---|---|---|---|---|
| | Calcurated value | EDS | | | |
| — | 0.81 | 0.84 | 15.46 | 9.46 | 162.9% |

Figure 6:
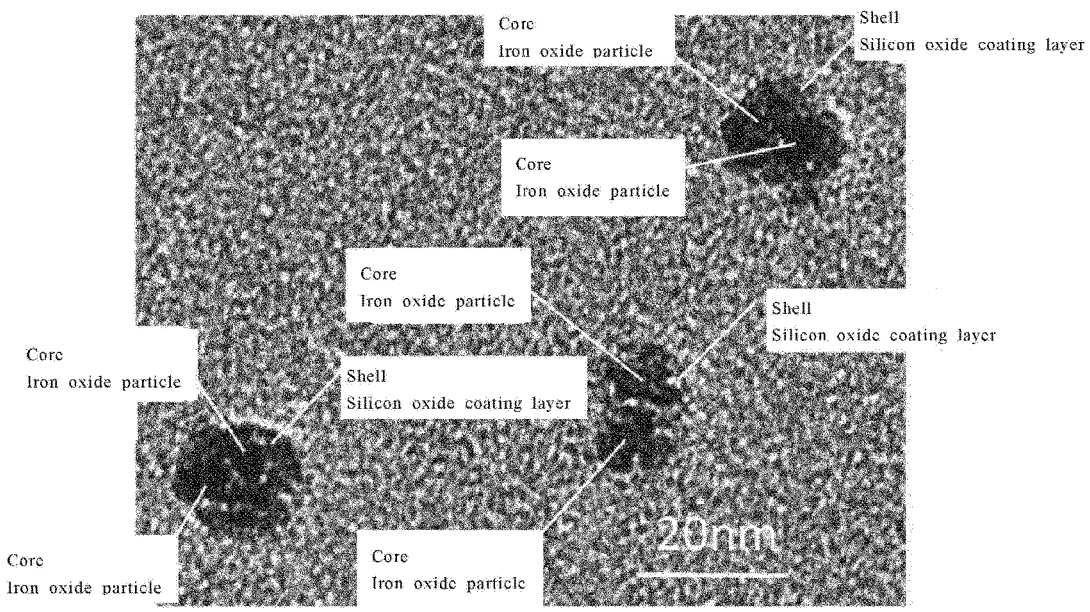
FIG. 6 shows a TEM photograph of the silicon oxide-coated iron oxide particles obtained in Example 4 of the present invention.

Then, the prepared iron oxide raw material liquid, the iron oxide precipitation solvent, and the silicon oxide raw material liquid were mixed in the same fluid processing apparatus as in Example 1. Table 4 shows the operating conditions of the fluid processing apparatus. The core conversion particle diameter (Dc) described in Table 4 is the maximum distance between two points on the outer periphery of the core iron oxide forming the aggregates, and, the average value of the results calculated from 100 aggregates is shown. The methods of washing, analysis and evaluation of particles are the same as in Example 1. A TEM photograph of the silicon oxide-coated iron oxide particles obtained in Example 4 is shown in FIG. 6. The core is an aggregate of a plurality of primary iron oxide particles, and the silicon oxide-coated iron oxide particles wherein the aggregates are coated with silicon oxide, was observed. The coating layer (shell) of the silicon oxide on the surface of the aggregates of iron oxide particles was observed. Regarding the state of the coating, it was also observed that the aggregates were mainly uniformly coated, but a part of the aggregates were not coated.

Further, the particle diameter of the silicon oxide-coated iron oxide particles obtained in Example 4 was 50 nm or less. Not shown details of the particle diameter D or the core particle diameter Dc in FIG. 6, but D/Dc was about 162.9%. In the XRD measurement results, peaks of $\alpha$-$Fe_2O_3$ (hematite) were detected as in Example 1, and the FT-IR measurement results were similar to those in Example 1.

In the XRD measurement results, peaks of $\alpha$-$Fe_2O_3$ (hematite) were clearly detected in all conditions in Examples 1 to 4 and Comparative Example 1. As described above, in Examples 1 to 4, peaks of silicon oxide coating on the surface of the particles were not detected, and thus, the silicon oxide is considered to be amorphous.

Comparative Example 2

The iron oxide raw material liquid, the iron oxide precipitation solvent, and the silicon oxide raw material liquid were prepared using the high-speed rotary dispersion emulsification apparatus CLEAMIX (product name: CLM-2.2 S, M. Technique Co., Ltd.). Specifically, based on the formulation of the iron oxide raw material liquid shown in Comparative Example 2 of Table 5, the components of the iron oxide raw material liquid were mixed homogeneously by stirring using CLEARMIX at preparation temperature of 40° C. and at the rotor rotational speed of 20000 rpm for 30 min to prepare the iron oxide raw material liquid. Based on the formulation of the iron oxide precipitation solvent shown in Comparative Example 2 of Table 5, the components of the iron oxide precipitation solvent were mixed homogeneously by stirring using CLEARMIX at preparation temperature of 45° C. and at the rotor rotational speed of 15000 rpm for 30 min to prepare iron oxide precipitation solvent. Furthermore, based on the formulation of the silicon oxide raw material liquid shown in Comparative Example 2 of Table 5, the components of the silicon oxide raw material liquid were mixed homogeneously by stirring using CLEARMIX at preparation temperature of 20° C. and at the rotor rotational speed of 6000 rpm for 10 min to prepare the silicon oxide raw material liquid.

Regarding the substances represented by the chemical formula and abbreviations set forth in Table 5, 60 wt % $HNO_3$ is concentrated nitric acid (Kishida Chemical Co., Ltd.), NaOH is sodium hydroxide (Kanto Chemical Co., Inc.), TEOS is tetraethyl orthosilicate (Wako Pure Chemical Industry Ltd.), and $Fe(NO_3)_3 \cdot 9H_2O$ is iron nitrate nonahydrate (Kanto Chemical Co., Inc.).

aggregate of primary particles of iron oxide as a core is coated with silicon oxide as a shell. The particles wherein the primary particle diameter of the iron oxide as a core cannot be recognized are also observed. Further, the diameter of the iron oxide aggregates (maximum distance between two points on outer periphery) in the silicon oxide-coated iron oxide particles obtained in Comparative Example 2, exceeds 50 nm. In the XRD measurement results, peaks of $\alpha$-$FeO_3$ (hematite) were detected as in Example 1, and the FT-IR measurement results were similar to those in Example 1.

Comparative Example 3

In Comparative Example 3, iron(III) oxide ($\alpha$-$Fe_2O_3$) produced by Wako Pure Chemical Industries, Ltd. was dispersed in propylene glycol or water in the same manner as in Example 1. A TEM observation, haze value, ultraviolet-visible absorption spectrum, reflection, spectrum and XRD were measured in the same manner as in Example 1.

TABLE 5

| Comparative Example 2 | | | | | | | | | | |
|---|---|---|---|---|---|---|---|---|---|---|
| Formulation of the 1st fluid (liquid A) Iron oxide raw material liquid | | | Formulation of the 2nd fluid (liquid B) Iron oxide precipitation solvent | | | | Formulation of the 3rd fluid (liquid C) — | | | |
| Formulation [wt %] | | | Formulation [wt %] | | | | Formulation [wt %] | | | |
| Raw material [wt %] | Raw material [wt %] | pH [° C.] | Raw material [wt %] | Raw material [wt %] | pH | | Raw material [wt %] | Raw material [wt %] | Raw material [wt %] | pH [° C.] |
| $Fe(NO_3)_3$ $9H_2O$ [2.00 wt %] | Pure water [98.00 wt %] | 1.8  26.6 | NaOH [9.00 wt %] | Pure water [91.00 wt %] | >14 | — | Pure water [97.52 wt %] | 60 wt % $HNO_3$ [2.11 wt %] | TEOS [0.37 wt %] | <1  — |

TABLE 6

| Comparative Example 2 | | | | | | | | | | |
|---|---|---|---|---|---|---|---|---|---|---|
| Introduction flow rate [ml/min] | | | Introduction temperature (liquid sending temperature) [° C.] | | | Introduction pressure (liquid sending pressure) [MPaG] | | | Discharged liquid | |
| Liquid A | Liquid B | Liquid C | Liquid A | Liquid B | Liquid C | Liquid A | Liquid B | Liquid C | pH | Temperature [° C.] |
| 400 | 50 | 50 | 143 | 83 | 25 | 0.329 | 0.50 | 0.50 | 12.99 | 23.4 |

Figure 9:
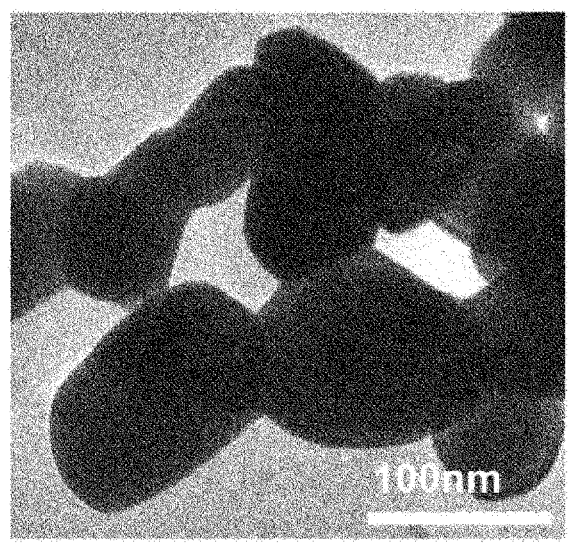
FIG. 9 shows a TEM photograph of the iron oxide particles of Comparative Example 3 of the present invention.

Then, the prepared iron oxide raw material liquid, the iron oxide precipitation solvent, and the silicon oxide raw material liquid were mixed in the same fluid processing apparatus as in Example 1. Table 6 shows the operating conditions of the fluid processing apparatus. The methods of washing, analysis and evaluation of particles are the same as in Example 1. As a result of TEM observation of the silicon oxide-coated iron oxide particles obtained in Comparative Example 2, iron oxide particles wherein the entire surface of one iron oxide particle is uniformly coated with silicon oxide, were not observed, and many particles wherein a plurality of iron oxide particles is coated with silicon oxide were observed. FIG. 5 shows a TEM photograph of the silicon oxide-coated iron oxide particles obtained in Comparative Example 2. As seen in FIG. 5, it is observed that the FIG. 9 shows a TEM photograph of the iron oxide particles of Comparative Example 3. The average primary particle diameter was 119.6 nm. In the production of a TEM observation sample of Comparative Example 3, the above commercially available iron(III) oxide ($\alpha$-$Fe_2O_3$) was used without washing. In the XRD measurement results, peaks of $\alpha$-$Fe_2O_3$ (hematite) were clearly detected.

The molar absorption coefficients were calculated from the absorbance obtained from the absorption spectrum measurement results of the dispersions wherein the silicon oxide-coated iron oxide particles obtained in Examples 1 and 4 in pure water, and of the dispersions wherein the iron oxide, particles of Comparative Examples 1 and 3 in propylene glycol, and the iron oxide concentration (as $Fe_2O_3$) in the measurement liquids. The graph showing the measurement wavelength on horizontal axis and the molar absorption coefficient on vertical axis is shown in FIG. 8. The average molar absorption coefficients at wavelengths in a range from 190 nm to 380 nm, and the molar absorption coefficients at a wavelength of 220, 250, 300, 350 and 400 nm are shown in Table 7 together with the pH and conductivity of the measurement liquids.

concentration of 2.0 wt % was 0.89%, and thus, it was a highly transparent dispersion. The haze value of the dispersion wherein the iron oxide particles of Comparative Example 3 was dispersed in propylene glycol at a $Fe_2O_3$ concentration of 0.02 wt % was 21.9%, and the haze value of the dispersion wherein the iron oxide particles of Comparative Example 3 was dispersed in pure water at a $Fe_2O_3$

TABLE 7

| | Molar absorption coeficient at each measurement wavelength [L/(mol · cm)] | | | | | | pH | | conductivity | |
|---|---|---|---|---|---|---|---|---|---|---|
| | Average molar absorption coeficient (190-380 nm) | 220 nm | 250 nm | 300 nm | 350 nm | 400 nm | pH | Measurement temperature [° C.] | [μS/cm] | Measurement temperature [° C.] |
| Example 1 | 4029 | 5549 | 4675 | 3646 | 2313 | 1561 | 6.91 | 25.2 | 2.21 | 25.2 |
| Example 2 | 3687 | 5391 | 4159 | 3051 | 2166 | 1156 | 6.89 | 25.1 | 2.26 | 25.1 |
| Example 3 | 2457 | 3538 | 2994 | 2342 | 1744 | 1023 | 6.94 | 25.4 | 2.16 | 25.4 |
| Example 4 | 2183 | 2989 | 2529 | 1979 | 1473 | 864 | 6.94 | 25.4 | 2.24 | 25.4 |
| Comparative Example 1 | 1013 | 1392 | 1177 | 920 | 681 | 395 | 6.97 | 25.6 | 2.21 | 25.6 |
| Comparative Example 2 | 1236 | 1705 | 1437 | 1120 | 824 | 478 | 6.97 | 25.1 | 2.29 | 25.1 |
| Comparative Example 3 | 82 | 128 | 76 | 72 | 68 | 71 | 6.97 | 25.6 | 2.28 | 25.6 |

The measurement results of the transmission spectra of the dispersions which were obtained by dispersing the silicon oxide-coated iron oxide particles obtained in Example 1 and. Example 4, and the iron oxide or the silicon oxide-coated iron oxide particles obtained in Comparative Example 1, Comparative Example 2 and Comparative Example 3 in pure water, and the measurement result of the transmission spectrum of the dispersion which was obtained by dispersing the silicon oxide-coated iron oxide particles obtained in Example 2 in butyl acetate are shown in FIG. 7. The iron oxide concentrations in the dispersions used for the measurement were the same. As seen in FIG. 7, almost no difference was observed between the transmittance in the visible region and the transmittance in the ultraviolet region in the dispersions using the silicon oxide-coated iron oxides and the iron oxides in Examples and Comparative Examples, except Comparative Example 3. However, as seen in FIG. 8 and Table 7, the average molar absorption coefficient of the silicon oxide-coated iron oxide composition for coating comprising the silicon oxide-coated iron oxides of Examples of the present invention, for the light of the wavelengths from 190 nm to 380 nm is 1500 L/(mol·cm) or more. But, the average molar absorption coefficient, of the iron oxide particles of Comparative Example 1, which surface is not coated with silicon oxide, and of the dispersion of the silicon oxide-coated iron oxide of Comparative Example 2, wherein at least a part of the surface of the iron oxide aggregates is coated with silicon oxide, wherein a diameter of the iron oxide aggregates exceeds 50 nm, for the light of the wavelengths from 190 nm to 380 nm is less than 1500 L/(mol·cm).

The haze value of the dispersion wherein the silicon oxide-coated iron oxide particles obtained in above Example 1 was dispersed in propylene glycol at a $Fe_2O_3$ concentration of 0.05 wt % was 0.00%, and the haze value of the dispersion wherein the particles obtained in Example 1 was dispersed in pure water at a $Fe_2O_3$ concentration of 0.31 wt % was 0.00%. Accordingly both dispersions were highly transparent dispersions. Further, the haze value of the dispersion wherein the silicon oxide-coated iron oxide particles obtained in Example 1 was dispersed in water at a $Fe_2O_3$ concentration of 0.31 wt % was 15.9%. Further, the haze value of the dispersion wherein the iron oxide particles of Comparative Example 3 was dispersed in pure water at a $Fe_2O_3$ concentration of 2.0 wt % was 23.4%, and obvious turbidity was observed. The haze value of the dispersion wherein the iron oxide particles obtained in Comparative Example 1 was dispersed in pure water at a $Fe_2O_3$ concentration of 2.0 wt % was 2.56%, and turbidity was observed. The haze value of the dispersion wherein the iron oxide particles of Comparative Example 2 was dispersed in propylene glycol at a $Fe_2O_3$ concentration of 0.02 wt % was 6.44%, and the haze value of the dispersion wherein the iron oxide particles of Comparative Example 2 was dispersed in pure water at a $Fe_2O_3$ concentration of 0.31 wt % was 7.9%, and the haze value of the dispersion wherein the iron oxide particles of Comparative Example 2 was dispersed in pure water at a $Fe_2O_3$ concentration of 2.0 wt % was 8.8%, and obvious turbidity was observed. The haze value of the dispersion wherein the silicon oxide-coated iron oxide particles obtained in above Example 2 was dispersed in butyl acetate at a $Fe_2O_3$ concentration of 0.05 wt % was 0.12%, and the haze value of the dispersion wherein the particles obtained in Example 2 was dispersed in butyl acetate at a $Fe_2O_3$ concentration of 0.31 wt % was 0.22%, and both were highly transparent dispersions. Further, the haze value of the dispersion wherein the particles obtained in Example 2 was dispersed in butyl acetate at a $Fe_2O_3$ concentration of 2.0 wt % was 1.26%, and it was a transparent dispersion.

The haze value of the dispersion wherein the silicon oxide-coated iron oxide particles obtained in above Example 3 was dispersed in propylene glycol at a $Fe_2O_3$ concentration of 0.05 wt % was 0.09%, and the haze value of the dispersion wherein the particles obtained in Example 3 was dispersed in pure water at a $Fe_2O_3$ concentration of 0.31 wt % was 0.14%, and both were highly transparent dispersions. Further, the haze value of the dispersion wherein the particles obtained in Example 3 was dispersed in pure water at a $Fe_2O_3$ concentration of 2.0 wt % was 0.54%, and it was a highly transparent dispersion.

The haze value of the dispersion wherein the silicon oxide-coated iron oxide particles obtained in above Example 4 was dispersed in propylene glycol at a $Fe_2O_3$ concentration of 0.05 wt % was 0.91%, and the haze value of the dispersion wherein the particles obtained in Example 4 was dispersed in pure water at a $Fe_2O_3$ concentration of 0.31 wt % was 1.46%, and it was a highly transparent dispersion, though it is not to the extent of a silicon oxide-coated iron oxide particles obtained in Example 1. Further, the haze value of the dispersion wherein the particles obtained in Example 4 is dispersed in pure water at a $Fe_2O_3$ concentration of 2.0 wt % is 1.64%, and it was a highly transparent dispersion, though it is not to the extent of a silicon oxide-coated iron oxide particles obtained in Example 1.

As shown above, the molar absorption coefficients of the silicon oxide-coated iron oxide particles obtained in Examples 1 to 4 or a composition thereof exceed 1500 L/(mol·cm) over a range from 190 nm to 380 nm. The silicon oxide-coated iron oxide particles obtained in Examples 1 to 4 or a composition thereof have a high ultraviolet protection ability when used in cosmetics or paints, and do not impair transparency texture or appearance when applied to a skin, or designability of a product when applied to a coated body, and thus, they can be used preferably. Thereby, the haze value of the composition for coating can be reduced, and a high transparency can be obtained. On the other hand, regarding the iron oxide particles of Comparative Examples 1 to 3, clear difference between the absorption region in the ultraviolet and visible region and the transmission region in the visible region was not recognized. Thus, the iron oxide particles impair coloring of the original coating material, color characteristics, textures or appearance, or designability of a product.

The invention claimed is:

1. A silicon oxide-coated iron oxide composition for coating comprising iron oxide particles, wherein a primary particle diameter of the iron oxide particles is 1 nm or more and 50 nm or less,
   wherein at least a part of the surface of said iron oxide particles is coated with silicon oxide,
   wherein at least a part of the surface of one iron oxide particle or the surface of an aggregate of a plurality of iron oxide particles is coated with silicon oxide, and the particle diameter of said iron oxide particle or said aggregate of iron oxide particles is 50 nm or less, and
   wherein said composition comprises an iron oxide particle dispersion having the average molar absorption coefficient of 1500 L/(mol·cm) or more for the light having wavelengths from 190 nm to 380 nm in a state that said coated iron oxide particles are dispersed in a dispersion medium.

2. The silicon oxide-coated iron oxide composition for coating according to claim 1, wherein said dispersion medium of the iron oxide particle dispersion is pure water.

3. The silicon oxide-coated iron oxide composition for coating according to claim 1, wherein said coated iron oxide particles are provided with an ester group, and said dispersion medium is butyl acetate.

4. The silicon oxide-coated iron oxide composition for coating according to claim 1, wherein
   the molar absorption coefficient of said iron oxide particle dispersion for the light having wavelength of 400 nm is 500 L/(mol·cm) or more, or
   the molar absorption coefficient of said iron oxide particle dispersion for the light having wavelength of 300 nm is 1500 L/(mol·cm) or more, or
   the molar absorption coefficient of said iron oxide particle dispersion for the light having wavelength of 250 nm is 1500 L/(mol·cm) or more.

5. The silicon oxide-coated iron oxide composition for coating according to claim 1, wherein the molar absorption coefficient of said iron oxide particle dispersion for the light having wavelength of 220 nm is 2000 L/(mol·cm) or more.

6. The silicon oxide-coated iron oxide composition for coating according to claim 1, wherein the transmittance of said iron oxide particle dispersion for the light having wavelengths from 200 nm to 420 nm is 2.0% or less, and
   wherein the transmittance of said iron oxide particle dispersion for the light having wavelengths from 620 nm to 780 nm is 80% or more.

7. The silicon oxide-coated iron oxide composition for coating according to claim 1, wherein the haze value of said iron oxide particle dispersion is 2.0% or less at the concentration of 2 wt % of silicon oxide-coated iron oxide.

8. The silicon oxide-coated iron oxide composition for coating according to claim 1, wherein said silicon oxide comprises amorphous silicon oxide.

9. The silicon oxide-coated iron oxide composition for coating according to claim 1, wherein said iron oxide particles coated with silicon oxide is core-shell type iron oxide particles wherein the surface of the core iron oxide particles is coated with the shell silicon oxide, and
   wherein the primary particle diameter of said core-shell type iron oxide particles is 100.5% or more and 190% or less relative to the primary particle diameter of said core iron oxide particles.

10. The silicon oxide-coated iron oxide composition for coating according to claim 1, wherein the particle diameter of said iron oxide particles coated with silicon oxide is 100.5% or more and 190% or less relative to said particle diameter of the iron oxide particle or said aggregate of the iron oxide particles.

11. The silicon oxide-coated iron oxide composition for coating according to claim 1, further comprising a perylene pigment.

12. A paint comprising the silicon oxide-coated iron oxide composition for coating according to claim 1.

13. A coating film comprising the silicon oxide-coated iron oxide composition for coating according to claim 1.

14. A vehicle equipped with the coating film according to claim 13.

* * * * *